(12) United States Patent
Matur et al.

(10) Patent No.: US 11,547,752 B2
(45) Date of Patent: Jan. 10, 2023

(54) MULTIVALENT PNEUMOCOCCAL VACCINE COMPOSITIONS COMPRISING POLYSACCHARIDE-PROTEIN CONJUGATES

(71) Applicant: BIOLOGICAL E LIMITED, Telangana (IN)

(72) Inventors: Ramesh Venkat Matur, Hyderabad (IN); Rajan Sriraman, Hyderabad (IN); Deviprasanna Chakka, Hyderabad (IN); Satyam Naidu Sureddi, Hyderabad (IN); Rajendar Burki, Hyderabad (IN); Sreenivasa Rao Ganti, Hyderabad (IN); Narender Dev Mantena, Hyderabad (IN); Mahima Datla, Hyderabad (IN)

(73) Assignee: BIOLOGICAL E LIMITED

( * ) Notice: Subject to any disclaimer, the term of this patent is extended or adjusted under 35 U.S.C. 154(b) by 1 day.

(21) Appl. No.: 16/369,933

(22) Filed: Mar. 29, 2019

(65) Prior Publication Data
US 2019/0224295 A1 Jul. 25, 2019

Related U.S. Application Data

(63) Continuation-in-part of application No. PCT/US2017/054237, filed on Sep. 29, 2017.

(30) Foreign Application Priority Data

Sep. 30, 2016 (IN) .............................. 201641033563

(51) Int. Cl.
*A61K 39/09* (2006.01)
*A61K 39/39* (2006.01)
(Continued)

(52) U.S. Cl.
CPC .......... *A61K 39/092* (2013.01); *A61K 9/0019* (2013.01); *A61K 39/385* (2013.01);
(Continued)

(58) Field of Classification Search
CPC .............. A61K 2039/70; A61K 9/0019; A61K 2039/6068; A61K 39/385;
(Continued)

(56) References Cited

U.S. PATENT DOCUMENTS 4,365,170 A 12/1982 Okuhara
4,673,574 A 6/1987 Anderson
(Continued)

FOREIGN PATENT DOCUMENTS

CN 101590224 12/2009
CN 103623401 3/2014
(Continued)

OTHER PUBLICATIONS

Whaley et al., Concomitant administration of recombinant PsaA and PCV7 reduces Streptococcus pneumoniae serotype 19A colonization in a murine model Vaccine. Volume 28, Issue 18, Apr. 19, 2010, pp. 3071-3075 (Year: 2010).*
(Continued)

*Primary Examiner* — Jana A Hines
(74) *Attorney, Agent, or Firm* — Perkins Coie LLP

(57) ABSTRACT

The present disclosure relates to multivalent pneumococcal vaccine compositions comprising capsular pneumococcal polysaccharide serotypes each individually conjugated to carrier proteins. When conjugated, the combination of the capsular pneumococcal polysaccharide serotype and the carrier protein is referred to herein as a polysaccharide-protein conjugate. The pneumococcal vaccine compositions may further comprise one or more of the following; a pharmaceutically acceptable carrier, a pharmaceutically
(Continued)

acceptable diluent, a buffer, a preservative, a stabilizer, an adjuvant, and/or a lyophilization excipient. Methods of making and administering the pneumococcal vaccine compositions described herein are also provided.

16 Claims, 16 Drawing Sheets

(51) Int. Cl.
A61K 39/385 (2006.01)
A61K 9/00 (2006.01)
A61K 39/00 (2006.01)
(52) U.S. Cl.
CPC .... A61K 39/39 (2013.01); A61K 2039/55505 (2013.01); A61K 2039/6068 (2013.01); A61K 2039/70 (2013.01)
(58) Field of Classification Search
CPC ........ A61K 2039/55505; A61K 39/092; A61K 39/39; A61P 27/16; A61P 11/00; A61P 37/04; A61P 29/00; A61P 25/00; A61P 31/04
See application file for complete search history.

(56) References Cited

U.S. PATENT DOCUMENTS

| | | | |
|---|---|---|---|
| 4,902,506 A | 2/1990 | Anderson et al. | |
| 5,360,897 A | 11/1994 | Anderson et al. | |
| 5,614,382 A | 3/1997 | Metcalf | |
| 5,693,326 A | 12/1997 | Lees | |
| 5,854,416 A | 12/1998 | Sampson et al. | |
| 7,862,823 B1 | 1/2011 | Leroy | |
| 7,955,605 B2 | 6/2011 | Prasad | |
| 8,192,746 B2 | 6/2012 | Caulfield et al. | |
| 8,465,749 B2 | 6/2013 | Lee et al. | |
| 8,557,250 B2 | 10/2013 | Lee | |
| 8,603,484 B2 | 12/2013 | Prasad | |
| 8,808,708 B2 | 8/2014 | Hausdorff et al. | |
| 2007/0253985 A1* | 11/2007 | Look | A61K 47/44 424/244.1 |
| 2009/0017059 A1 | 1/2009 | Biemans et al. | |
| 2010/0074922 A1* | 3/2010 | Biemans | A61P 11/00 424/238.1 |
| 2010/0239604 A1 | 9/2010 | Biemans et al. | |
| 2012/0321658 A1 | 12/2012 | Biemans et al. | |
| 2015/0343076 A1 | 12/2015 | Park et al. | |

FOREIGN PATENT DOCUMENTS

| | | | |
|---|---|---|---|
| CN | 103656631 | 3/2014 | |
| CN | 103656632 | 3/2014 | |
| CN | 104069488 | 10/2014 | |
| EP | 2425856 | 3/2012 | |
| EP | 3296741 * | 8/2019 | ........... G01N 33/569 |
| IN | 140/DEL/2011 | 8/2012 | |
| IN | 140/DEL/2011 A * | 8/2013 | |
| WO | WO 1993/015760 | 8/1993 | |
| WO | WO 1995/008348 | 3/1995 | |
| WO | WO 1996/029094 | 9/1996 | |
| WO | WO 1998/042721 | 10/1998 | |
| WO | WO-2007071707 A2 * | 6/2007 | ................ A61P 7/00 |
| WO | WO 2009/00826 | 12/2008 | |
| WO | WO 2010/120921 | 10/2010 | |
| WO | WO 2011/110241 | 9/2011 | |
| WO | WO 2011/151841 | 12/2011 | |
| WO | WO 2013/191459 | 12/2013 | |
| WO | WO 2014/092377 | 6/2014 | |
| WO | WO 2014/092378 | 6/2014 | |
| WO | WO 2016/079755 | 5/2016 | |
| WO | WO 2016/174683 | 11/2016 | |
| WO | WO 2016/207905 | 12/2016 | |
| WO | WO-2016207905 A2 * | 12/2016 | ........... A61K 9/0043 |

OTHER PUBLICATIONS

AlonsoDeVelasco et al. "Streptococcus pneumoniae: Virulence factors, pathogenesis, and vaccines," Microbiological Reviews, 59(4):591-603 (publication date: Dec. 1, 1995).
Anderson et al., "Non-interference between two protein carriers when used with the same polysaccharide for pneumococcal conjugate vaccines in 2-year-old children," Vaccine, 21 (13-14):1554-9) (publication date: Mar. 28, 2003, epublication date: Nov. 8, 2002).
Bethell et al., "A novel method of activation of cross-linked agarose with 1,1'-carbonyldiimidazole which gives a matrix for affinity chromatography devoid of additional charged groups," Journal of Biological Chemistry, 254(8):2572-4 (publication date: Apr. 25, 1979).
Chu et al., "Further Studies on the Immunogenicity of Haemophilus influenzae Type b and Pneumococcal Type 6A Polysaccharide-Protein Conjugates," Infection and Immunity, 40(1):245-256 (publication date: Apr. 1983).
Crain et al. "Pneumococcal surface protein A (PspA) is serologically highly variable and is expressed by all clinically important capsular serotypes of Streptococcus pneumoniae," Infection and Immunity, 58(10):3293-3299 (publication date: Oct. 1990).
Gatchalian et al., "A randomized, placebo-controlled study to evaluate the immunogenicity of an 11-valent pneumococcal protein D conjugate vaccine administered as primary vaccination to infants at 6, 10, and 14 weeks of age," Abstract of the 19th Annual Meeting of the European Society for Pediatric Infectious Diseases (ESPID), (Istanbul) (publication date: Mar. 26-28, 2001).
Hearn et al., "Application of 1,1'-carbonyldiimidazole-activated matrices for the purification of proteins. III. The use of 1,1'-carbonyldiimidazole-activated agarose in the biospecific affinity chromatography isolation of serum antibodies," Journal of Chromatography, 218:509-18 (publication date: Nov. 20, 1981, epublication date: Nov. 1, 2001).
International Search Report and Written Opinion dated Nov. 16, 2017 for International Application No. PCT/US2017/054237.
Larentis et.al, "Cloning and optimization of induction conditions for mature PsaA (pneumococcal surface adhesin A) expression in Escherichia coli and recombinant protein stability during long-term storage," Protein expression and Purification, 78(1):38-47 (publication date: Jul. 2011, epublication date: Mar. 6, 2011).
Lin et al., "Preparation and immunogenicity of capsular polysaccharide-surface adhesin A (PsaA) conjugate of Streptococcus pneumoniae," Immunobiology, 215(7):545-50 (publication date: Jul. 2010, epublication date: Oct. 31, 2009).
McDaniel et al. "PspA, a surface protein of Streptococcus pneumoniae, is capable of eliciting protection against pneumococci of more than one capsular type," Infection and Immunity, 59(1):222-228 (publication date: Jan. 1991).
Miyaji EN et al., "PsaA (Pneumococcal surface adhesin A) and PspA (pneumococcal surface protein A) DNA vaccines induce humoral and cellular immune responses against Streptococcus pneumoniae," Vaccine, 20(5-6):805-12 (publication date: Dec. 12, 2001, epublication date: Dec. 3, 2001).
Nurkka et al. "Immunogenicity and Safety of the Eleven Valent Pneumococcal Polysaccharide-Protein D Conjugate Vaccine in Infants," The Pediatric Infectious Disease Journal, 23(11):1008-1014 (publication date: Nov. 1, 2004).
Paton et al. "Effect of immunization with pneumolysin on survival time of mice challenged with Streptococcus pneumoniae," Infection and Immunity, 40(2):548-552 (publication date: May 1983).
Sucher et al., "Prevnar 13, the New 13-Valent Pneumococcal Conjugate Vaccine," The Annals of Pharmacotherapy, 45(12):1516-1524 (publication date: Dec. 2011, epublication date: Nov. 1, 2011).
Talkington et al., "Protection of mice against fatal pneumococcal challenge by immunization with pneumococcal surface adhesin A (PsaA)," Microbial Pathogenesis, 21(1):17-22 (publication date: Jul. 1996, epublication date: May 25, 2002).
Wuorimaa et al. "Tolerability and immunogenicity of an eleven-valent pneumococcal conjugate vaccine in healthy toddlers," The

(56) References Cited

OTHER PUBLICATIONS

Pediatric Infectious Disease Journal, 20(3):272-277 (publication date: Mar. 2001).

* cited by examiner

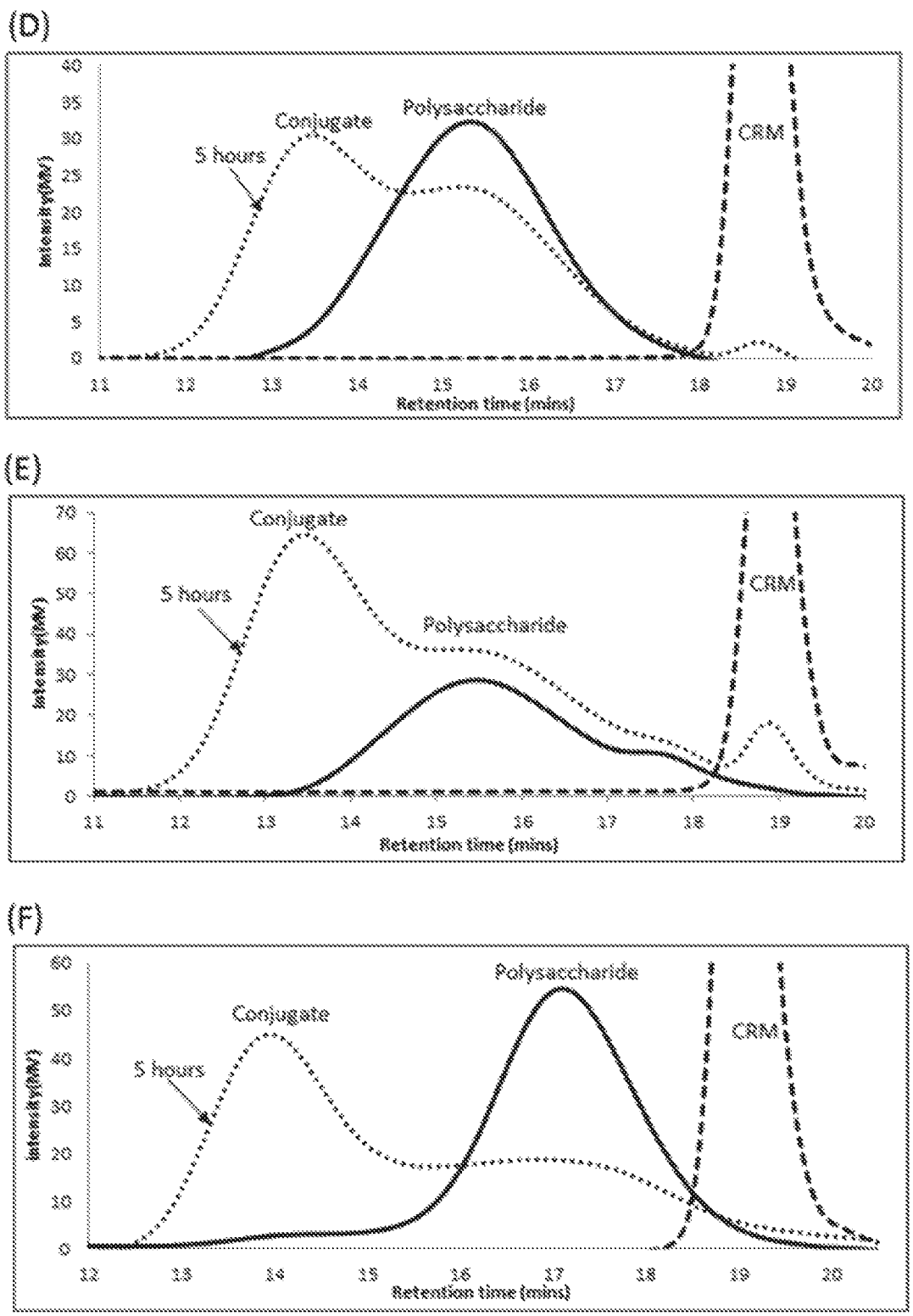
FIG. 1 (contd.)

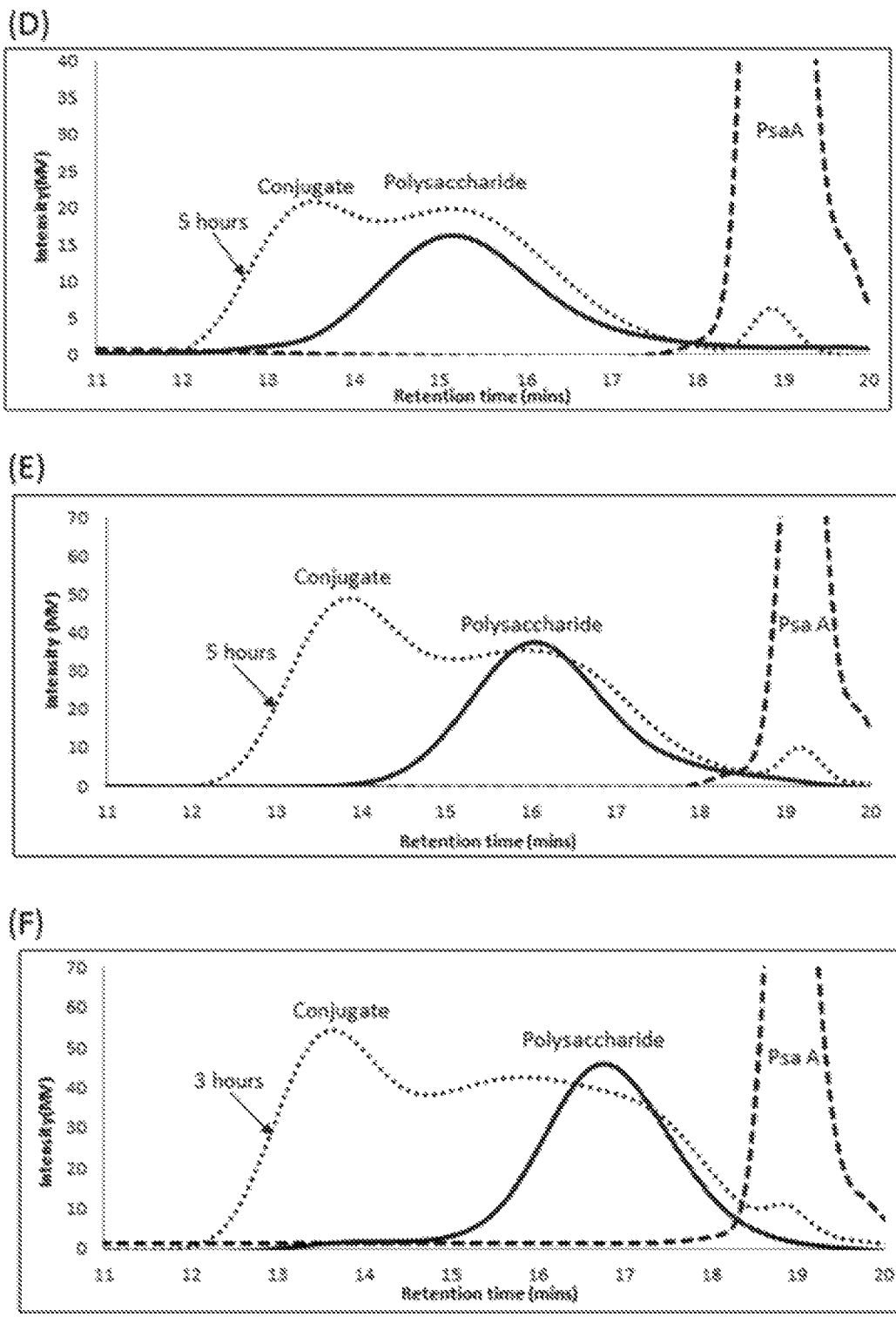
FIG. 2 (contd.)

MULTIVALENT PNEUMOCOCCAL VACCINE COMPOSITIONS COMPRISING POLYSACCHARIDE-PROTEIN CONJUGATES

CROSS-REFERENCE TO RELATED APPLICATION

This application is a continuation-in-part of International Application No. PCT/US2017/054237, filed on Sep. 29, 2017, which claims priority to Indian Patent Application No. 201641033563, filed on Sep. 30, 2016, their entire contents are incorporated herein by reference and relied upon.

TECHNICAL FIELD

The present disclosure relates to multivalent pneumococcal vaccine compositions comprising capsular pneumococcal polysaccharide of one or more *Streptococcus pneumoniae* serotypes conjugated to one or more carrier proteins. When conjugated, the capsular pneumococcal polysaccharide and the carrier protein is referred to herein as a polysaccharide-protein conjugate.

BACKGROUND

*Streptococcus pneumoniae* ("pneumococcus") is a gram-positive bacteria that causes invasive diseases, such as pneumonia, bacteremia and meningitis, and diseases associated with colonization, such as acute otitis media (e.g., colonization of middle ear). These pneumococcus-induced diseases result in morbidity and mortality, particularly in persons less than 24 months old and greater than 60 years old. The rate of pneumococcal pneumonia in the U.S. for persons over 60 years of age is estimated to be 3 to 8 per 100,000. In 20% of cases, pneumococcal pneumonia leads to bacteremia and meningitis collectively having a mortality rate close to 30% despite antibiotic treatment.

Proteins such as pneumolysin and the pneumococcal surface protein A (PspA) have been evaluated for their suitability as carrier protein candidates in pneumococcal vaccines. While both are partially protective in mice (Paton et al. "Effect of immunization with pneumolysin on survival time of mice challenged with *Streptococcus pneumoniae*." Infect Immun. 1983 May; 40(2): 548-552 and McDaniel et al. "PspA, a surface protein of *Streptococcus pneumoniae*, is capable of eliciting protection against pneumococci of more than one capsular type" Infect Immun. 1991 January; 59(1): 222-228.), there are disadvantages to their use as immunogens in vaccines. Pneumolysin, although well conserved among pneumococci, has toxic effects in its native state (AlonsoDeVelasco et al. "*Streptococcus pneumoniae*: Virulence factors, pathogenesis, and vaccines." Microbiol Rev. 1995 December; 59(4): 591-603.). On the other hand, PspA is serologically and structurally heterogeneous. (Crain et al. "Pneumococcal surface protein A) is serologically highly variable and is expressed by all clinically important capsular serotypes of *Streptococcus pneumoniae*." Infect Immun. 1990 October; 58(10): 3293-3299). Its use in vaccine formulations would require multiple PspA types, thus increasing the complexity of vaccine preparation.

Pneumococcal surface adhesion A ("PsaA") is a multifunctional lipoprotein and is involved in host cell adherence and colonization. It is a highly conserved surface protein and 97% homologous across known serotypes of *S. pneumoniae*. PsaA is immunogenic and anti-PsaA antibodies are known to increase during natural nasopharyngeal colonization of pneumococci.

Pneumococcal vaccines may be administered to prevent infections. Current vaccines include multivalent pneumococcal polysaccharide vaccines (comprises pneumococcal polysaccharides from two or more serotypes) and pneumococcal conjugate vaccines. The protective efficacy of the pneumococcal polysaccharide vaccine is known to be related to the concentration of antibody generated against a capsular polysaccharide. Pneumococcus cells are encapsulated with a polysaccharide giving rise to more than 90 different pneumococcus serotypes. The capsule is the principal virulence determinant for pneumococci—it not only protects the cell's inner surface from complement mediated cell lysis, it is also poorly immunogenic.

Merck's Pneumovax®23 is a multivalent pneumococcal polysaccharide vaccine and contains unconjugated capsular polysaccharides from 23 pneumococcal serotypes including serotypes 1, 2, 3, 4, 5, 6B, 7F, 8, 9N, 9V, 10A, 11A, 12F, 14, 15B, 17F, 18C, 19F, 19A, 20, 22F, 23F and 33F. In addition to Pneumovax®23, the multivalent pneumococcal polysaccharide vaccines that have been licensed thus far proved valuable in preventing pneumococcal disease in adults, particularly, the elderly and those at high-risk. However, infants and young children respond poorly to these unconjugated pneumococcal polysaccharide vaccines.

Prevnar®-7 is a pneumococcal polysaccharide-protein conjugate vaccine and includes the seven most frequently isolated polysaccharide serotypes (e.g., 4, 6B, 9V, 14, 18C, 19F, and 23F conjugated to $CRM_{197}$). Since use of Prevnar®-7 began in the United States in 2000, there has been a significant reduction in invasive pneumococcal disease (IPD) in children. A 13-valent conjugate vaccine Prevenar-13®, containing thirteen serotypes 1, 3, 4, 5, 6A, 6B, 7F, 9V, 14, 18C, 19A, 19F and 23F conjugated to $CRM_{197}$, was developed and approved due to the limitations in serotype coverage with Prevnar®-7 in certain regions of the world.

Synflorix® is a pneumococcal vaccine that includes ten polysaccharide serotypes—serotypes 1, 4, 5, 6B, 7, 9, 14, 23F—conjugated to protein D (PD), serotype 18C conjugated to tetanus toxoid (TT) and serotype 19F conjugated to diphtheria toxoid (DT). Each of the serotype polysaccharides are coupled utilizing 1-cyano-4-dimethylamino-pyridinium tetrafluoroborate (CDAP) under controlled pH.

Despite these vaccines, there is a need for additional multivalent pneumococcal vaccines comprising alternative polysaccharide serotypes and carrier proteins, as well as simple and efficient production thereof.

Pneumococcal vaccines have been described in additional references. For example, U.S. Pat. No. 5,360,897 discloses an immunogenic conjugate comprising a reductive amination product of an intact capsular polymer of the bacterial pathogen *S. pneumoniae* having at least two carbonyl groups and a bacterial toxin or toxoid, said conjugate comprising a cross-linked conjugate in which there is a direct covalent linkage between the capsular polymer and the toxin or toxoid.

U.S. Pat. No. 5,693,326 provides a generalized method for preparing a conjugate vaccine wherein for activating viral, fungal or bacterial polysaccharides, an organic cyanylating agent is used selected from the group 1-cyano-4-(dimethylamino)-pyridinium tetrafluoroborate, N-cyanotriethyl-ammonium tetrafluoroborate, and p-nitrophenylcyanate, to form an activated carbohydrate and is subsequently coupled to the protein or carrier protein.

U.S. Pat. No. 5,854,416 discloses amino acid and DNA sequences of 37-kDa protein from *S. pneumonia* known as PsaA (Pneumococcal surface adhesion A) and U.S. Pat. No. 7,862,823 discloses a multivalent conjugate vaccine composition comprising pneumococcal capsular polysaccharides with at least two different carrier proteins, such as DT and TT.

U.S. Pat. No. 7,955,605 describes a process of making immunogenic conjugate consisting 19A where the activated serotype 19A polysaccharide and carrier protein are resuspended in dimethyl sulfoxide (DMSO) to form a conjugate.

U.S. Pat. No. 8,192,746 discloses a 15-valent pneumococcal polysaccharide-protein conjugate vaccine composition having capsular polysaccharides from serotypes 1, 3, 4, 5, 6A, 6B, 7F, 9V, 14, 18C, 19A, 19F, 22F, 23F, and 33F conjugated to $CRM_{197}$.

U.S. Pat. No. 8,465,749 provides a method for preparing a conjugate vaccine by reacting a polysaccharide with CDAP and reacting a protein with hydrazine or adipic acid dihydrazide with specific pH range.

U.S. Pat. No. 8,557,250 B2 discloses a method comprising contacting a mixture of a plurality of cyanate activated immunogenic distinct polysaccharides with at least one hydrazide activated protein.

U.S. Pat. Nos. 8,808,708, 7,955,605 and 8,603,484 describe a 13-valent immunogenic composition consisting polysaccharide-protein conjugates where serotypes consist of 1, 3, 4, 5, 6A, 6B, 7F, 9V, 14, 18C, 19A, 19F and 23F, and carrier protein $CRM_{197}$.

U.S. Patent Publication No. 2009/0017059 A1 discloses an immunogenic composition wherein serotypes 19A and 19F are conjugated to different bacterial toxoids including tetanus toxoid, diphtheria toxoid, pertussis toxoid, bacterial cytolysins and/or pneumolysin.

U.S. Patent Publication No. 2010/0074922 A1 discloses an immunogenic composition containing 10 or more serotypes wherein 19F capsular saccharide is conjugated to DT, serotype 18C capsular saccharide is conjugated to tetanus toxoid and serotypes 1, 4, 5, 6B, 7F, 9V, 14 and 23F capsular saccharides are conjugated to Protein D isolated from *Haemophilus influenzae*.

U.S. Patent Publication No. 2010/0239604 describes an immunogenic composition comprising multivalent *S. pneumoniae* capsular saccharide conjugates from serotypes 19A and 19F wherein serotype 19A is conjugated to a first bacterial toxoid and 19F is conjugated to a second bacterial toxoid and 2-9 of the *S. pneumoniae* capsular saccharides are conjugated to protein D.

U.S. Patent Publication No. 2012/321658 A1 discloses an immunogenic composition wherein serotypes 1, 3, 19A and 19F linked to protein carrier(s) either directly or indirectly through a chemistry other than reductive amination, and one or more different saccharides is/are selected from a second group consisting of serotypes 4, 5, 6A, 6B, 7F, 9V, 14, 18C and 23F which is/are linked to a protein carrier(s) by reductive amination.

IN 140/DEL/2011 provides a *S. pneumonia* vaccine comprising either of (a) 7 or more (b) 10 or more polysaccharides from different serotypes conjugated to at least 2 or more carrier proteins selected from a group comprising DT, diphtheria toxoid, $CRM_{197}$, and tetanus toxoid.

WO Publication No. 2013/191459 A1 discloses a conjugated 15 valent composition comprising different serotypes of *S. pneumoniae* derived from a capsular polysaccharide 1, 2, 3, 4, 5, 6A, 6B, 7F, 9N, 9V, 14, 18C, 19A, 19F and 23F conjugated to $CRM_{197}$.

WO Publication No. 2014/092377 A1 discloses a 13 valent composition wherein 12 serotypes are selected from 1, 3, 4, 5, 6A, 6B, 7F, 9V, 14, 18C, 19A, 19F, and 23F and the last serotype is either 12 or 9N conjugated to $CRM_{197}$.

WO Publication No. 2014/092378 A1 describes an immunogenic conjugate composition where 12 serotypes are selected from 1, 3, 4, 5, 6A, 6B, 7F, 9V, 14, 18C, 19A, 19F, and 23F and remaining one from 22F or 33F conjugated to $CRM_{197}$.

WO 2016207905 A2 discloses a multivalent Pneumococcal conjugate vaccine (PCV) composition comprising: 1) at least 12 capsular polysaccharides selected from serotypes 1, 3, 4, 5, 6B, 7F, 9N, 9V, 15B, 14, 18C, 19A, 19F, 22F, 23F and 33F of *S. pneumoniae* activated with CDAP and conjugated to carrier protein $CRM_{197}$, and 2) a pharmaceutically acceptable carrier, wherein the composition does not contain capsular polysaccharide from serotype 6A.

Chinese Patent Application Publication No. CN 101590224 describes a 14 valent pneumococcal polysaccharide-protein conjugate vaccine containing serotypes 1, 2, 4, 5, 6A, 6B, 7F, 9N, 9V, 14, 18C, 19A, 19F and 23F conjugated to $CRM_{197}$.

Chinese Patent Application Publication No. CN 103623401 discloses a 14 multivalent pneumococcal capsular polysaccharide—protein conjugate composition wherein said 14 different serotype are 1, 3, 4, 5, 6A, 6B, 9V, 14, 18C, 19A, 19F, 22F, 23F and 33F conjugated to $CRM_{197}$.

Chinese Patent Application Publication No. CN 103656632 discloses a multivalent pneumococcal capsular polysaccharide composition containing serotype 6A and at least one extra serotype selected from the group consisting of 1, 2, 3, 4, 5, 6B, 7F, 8, 9N, 10A, 11A, 12F, 14, 15B, 17F, 18C, 19A, 19F, 20, 22F, 23F and 33F conjugated to $CRM_{197}$.

Chinese Patent Application Publication No. CN 103656631 provides a multivalent pneumococcus capsular polysaccharide-protein conjugate composition and a preparation method thereof. The conjugate composition is prepared from capsular polysaccharides of pneumococcus of 24 different serotypes and a carrier protein in a covalent linkage manner, wherein the 24 different serotypes are 1, 2, 3, 4, 5, 6A, 6B, 7F, 8, 9N, 9V, 10A, 11A, 12F, 14, 15B, 17F, 18C, 19A, 19F, 20, 22F, 23F and 33F conjugated to $CRM_{197}$.

Chinese Patent Application Publication No. CN 104069488 discloses a multivalent pneumococcus capsular polysaccharides of 14 different serotypes and carrier protein, wherein the 14 serotypes include 1, 4, 5, 6A, 6B, 7F, 9V, 14, 18C, 19A, 19F, 22F, 23F and 33F conjugated to $CRM_{197}$.

Deborah et al, (1996, Volume 21, Issue 1, Pages 17-22) describes PsaA as having significant homology with fimbrial adhesion proteins. Immunization of CBA/CaHNJ Xid mice with PsaA using either complete Freund's or TiterMax™ adjuvants significantly protected mice against heterologous intravenous challenge with type 3 pneumococcal strain WU2 at doses up to 45 times the $LD_{50}$.

Miyaji E N et al, (2001, Vaccine; 20 (5-6): 805-12) discloses *S. pneumoniae* as one of the most important human pathogens. DNA vaccine vectors containing either the full-length PsaA or a truncated PspA gene were constructed. Both constructs showed transient expression of the antigens in vertebrate cells and induced significant antibody response to the pneumococcal antigens in BALB/c mice injected intramuscularly.

Wuorimaa et al. (2001, The Paediatric Infectious Disease Journal, Volume 20(3), pp 272-277) discloses a study to assess the tolerability and immunogenicity in healthy toddlers of an 11-valent pneumococcal conjugate vaccine that uses both TT and DT as carriers.

Gatchalian et al. (2001, 17th Annual Meeting of the Eur. Soc. Paed. Inf. Dis (ESPID), poster number 4, P1A Poster Session 1, Istanbul Turkey) discloses an opsanophagocytic assay (OPA) results from infants who had received doses of the 11-valent vaccine failed to show antibody responses for serotype 3 at levels comparable to other tested serotypes.

Anderson P et al, (2003, Vaccine; 21 (13-14):1554-9) discloses a comparative study of tetravalent conjugate vaccines with each polysaccharide types 6A, 14, 19F, and 23F separately coupled to tetanus toxoid or diphtheria $CRM_{197}$ or a mixture of halved doses of polysaccharide types 6A, 14, 19F. and 23F separately coupled to tetanus toxoid and diphtheria $CRM_{197}$.

Nurkka et al. (2004, Ped. Inf. Dis. J., 23:1008-1014) discloses a study of the immunogenicity and safety of an 11-valent pneumococcal protein D conjugate vaccine where no priming effect was observed for serotype 3 in infants who had received three doses of the vaccine followed by a booster dose of either the same vaccine or a pneumococcal polysaccharide vaccine.

The above mentioned references disclose, amongst other compositions, methods, and the like, multivalent pneumococcal vaccines comprising polysaccharides from one or more serotypes as well as conjugation of these polysaccharides with carrier proteins such as $CRM_{197}$, protein D, DT, and TT. In view of the different serotypes that are prevalent across various regions, there is a need for additional multivalent pneumococcal vaccines comprising novel conjugates of polysaccharide serotypes with improved immune response, as well as simple and efficient production thereof.

SUMMARY

In several embodiments, the present disclosure provides a pneumococcal vaccine composition, the composition comprising two or more capsular pneumococcal polysaccharide serotypes each individually conjugated to pneumococcal surface adhesion protein A (PsaA) or combination of PsaA and $CRM_{197}$ as carrier proteins.

In one embodiment, the present disclosure provides a pneumococcal vaccine composition that is a 10 valent, 14 valent, 15 valent, 17 valent, 18 valent, 19 valent, 20 valent, 22 valent, 23 valent, 24 valent, or 25 valent pneumococcal vaccine composition.

In another embodiment, the present disclosure provides a pneumococcal vaccine composition comprising pneumococcal polysaccharides that are each serotypes selected from pneumococcal serotypes 1, 2, 3, 4, 5, 6A, 6B, 6C, 7F, 8, 9N, 9V, 10A, 11A, 12F, 14, 15A, 15B, 15C, 16F, 17F, 18C, 19F, 19A, 20A, 20B, 22F, 23A, 23B, 23F, 24B, 24F, 31, 33F, 34, 35B, 35F, 38, 39, and 45.

In another embodiment, the present disclosure provides a pneumococcal vaccine composition comprising pneumococcal polysaccharides from each serotypes selected from pneumococcal serotypes 1, 2, 3, 4, 5, 6A, 6B, 6C, 7F, 8, 9N, 9V, 10A, 11A, 12F, 14, 15A, 15B, 15C, 16F, 17F, 18C, 19F, 19A, 20A, 20B, 22F, 23A, 23B, 23F, 24B, 24F, 31, 33F, 34, 35B, 35F, 38, 39, and 45 conjugated with pneumococcal surface adhesion protein A (PsaA) as a carrier protein.

In another embodiment, the present disclosure provides a pneumococcal vaccine composition comprising pneumococcal polysaccharides from serotypes selected from 1, 2, 3, 4, 5, 6A, 6B, 6C, 7F, 8, 9N, 9V, 10A, 11A, 12F, 14, 15A, 15B, 15C, 16F, 17F, 18C, 19F, 19A, 20A, 20B, 22F, 23A, 23B, 23F, 24B, 24F, 31, 33F, 34, 35B, 35F, 38, 39, and 45 conjugated with pneumococcal surface adhesion protein A (PsaA) or combination of PsaA and $CRM_{197}$ as carrier proteins.

In another embodiment, the present disclosure provides a pneumococcal vaccine composition comprising pneumococcal polysaccharides from serotypes selected from 1, 2, 3, 4, 5, 6A, 6B, 6C, 7F, 8, 9N, 9V, 10A, 11A, 12F, 14, 15A, 15B, 15C, 16F, 17F, 18C, 19F, 19A, 20A, 20B, 22F, 23A, 23B, 23F, 24B, 24F, 31, 33F, 34, 35B, 35F, 38, 39, and 45 wherein at least 3 pneumococcal polysaccharides are conjugated with pneumococcal surface adhesion protein A (PsaA).

In another embodiment, the present disclosure provides a pneumococcal vaccine composition comprising pneumococcal polysaccharides from serotypes 3, 6A, 6B conjugated with pneumococcal surface adhesion protein A (PsaA).

In another embodiment, the present disclosure provides a pneumococcal vaccine composition comprising at least 10 pneumococcal polysaccharides selected from serotypes 1, 2, 3, 4, 5, 6A, 6B, 6C, 7F, 8, 9N, 9V, 10A, 11A, 12F, 14, 15A, 15B, 15C, 16F, 17F, 18C, 19F, 19A, 20A, 20B, 22F, 23A, 23B, 23F, 24B, 24F, 31, 33F, 34, 35B, 35F, 38, 39 and 45 and the carrier proteins comprise PsaA, or combination of PsaA and $CRM_{197}$.

In another embodiment, the present disclosure provides a pneumococcal vaccine composition comprising at least 14 pneumococcal polysaccharide conjugates.

In another embodiment, the present disclosure provides a pneumococcal vaccine composition comprising at least 17 pneumococcal polysaccharide conjugates.

In another embodiment, the present disclosure provides a pneumococcal vaccine composition comprising at least 19 pneumococcal polysaccharide conjugates.

In another embodiment, the present disclosure provides a pneumococcal vaccine composition comprising at least 20 pneumococcal polysaccharide conjugates.

In another embodiment, the present disclosure provides a pneumococcal vaccine composition comprising at least 22 pneumococcal polysaccharide conjugates.

In another embodiment, the present disclosure provides a pneumococcal vaccine composition comprising at least 24 pneumococcal polysaccharide conjugates.

In another embodiment, the present disclosure provides a pneumococcal vaccine composition comprising pneumococcal polysaccharides of two or more serotypes and a carrier protein, wherein the serotypes are selected from 3, 5, 6A, 6B, 9V and 18C, and the carrier protein is PsaA.

In another embodiment, the present disclosure provides a pneumococcal vaccine composition comprising pneumococcal polysaccharides of two or more serotypes and a carrier protein, wherein the serotypes are selected from 1, 3, 4, 5, 6A, 6B, 7F, 9V, 14, 18C, 19F, 19A and 22F and the carrier protein is PsaA.

In another embodiment, the present disclosure provides a pneumococcal vaccine composition comprising pneumococcal polysaccharides of two or more serotypes and a carrier protein, wherein the serotypes are selected from 1, 3, 4, 5, 6A, 6B, 7F, 9V, 10A, 12F, 14, 15A, 15B, 18C, 19F, 19A, 22F, 23F, 33F, 34, 35, 38 and 45, and the carrier protein is PsaA.

In another embodiment, the present disclosure provides a pneumococcal vaccine composition comprising pneumococcal polysaccharides of one or more serotypes and a carrier protein, wherein the serotypes are 1, 2, 3, 4, 5, 6A, 6B, 6C, 7F, 8, 9N, 9V, 10A, 11A, 12F, 14, 15A, 15B, 15C, 16F, 17F, 18C, 19F, 19A, 20A, 20B, 22F, 23A, 23B, 23F, 24B, 24F, 31, 33F, 34, 35B, 35F, 38, 39 and 45, and the carrier protein is PsA.

In another embodiment, the present disclosure provides a pneumococcal vaccine composition comprising pneumococcal polysaccharides of one or more serotypes and a carrier protein wherein the pneumococcal polysaccharides are each individually conjugated to PsaA or combination of PsaA and $CRM_{197}$.

In another embodiment, the present disclosure provides a pneumococcal vaccine composition comprising at least six pneumococcal polysaccharides each individually conjugated to PsaA, and one or more pneumococcal polysaccharides each individually conjugated to $CRM_{197}$.

In another embodiment, the present disclosure provides a pneumococcal vaccine composition comprising at least five pneumococcal polysaccharides each individually conjugated to PsaA, and at least five pneumococcal polysaccharides each individually conjugated to $CRM_{197}$.

In another embodiment, the present disclosure provides a 14 valent pneumococcal vaccine comprising at least five pneumococcal polysaccharides each individually conjugated to PsaA, and at least five pneumococcal polysaccharides each individually conjugated to $CRM_{197}$.

In another embodiment, the present disclosure provides a 17 valent pneumococcal vaccine comprising at least five serotypes of pneumococcal polysaccharides each individually conjugated to PsaA, and at least five serotypes of pneumococcal polysaccharides each individually conjugated to $CRM_{197}$.

In another embodiment, the present disclosure provides a 20 valent pneumococcal vaccine comprising at least five serotypes of pneumococcal polysaccharides each individually conjugated to PsaA, and at least five serotypes of pneumococcal polysaccharides each individually conjugated to $CRM_{197}$.

In another embodiment, the present disclosure provides a 22 valent pneumococcal vaccine comprising at least five serotypes of pneumococcal polysaccharides each individually conjugated to PsaA, and at least five serotypes of pneumococcal polysaccharides each individually conjugated to $CRM_{197}$.

In another embodiment, the present disclosure provides a 24 valent pneumococcal vaccine comprising at least five serotypes of pneumococcal polysaccharides each individually conjugated to PsaA, and at least five serotypes of pneumococcal polysaccharides each individually conjugated to $CRM_{197}$.

In another embodiment, the present disclosure provides a 14 valent pneumococcal vaccine comprising pneumococcal polysaccharide serotypes 1, 3, 4, 5, 6B, 7F, 9V, 14, 18C, 19A, 19F, 22F, 23F and 33F, wherein at least serotypes 3, and 6B are conjugated to PsaA and one or more serotypes 1, 4, 5, 7F, 9V, 14, 18C, 19A, 19F, 22F, 23F and 33F are conjugated to $CRM_{197}$.

In another embodiment, the present disclosure provides a 14 valent pneumococcal vaccine comprising pneumococcal polysaccharide serotypes 1, 3, 4, 5, 6A, 7F, 9V, 14, 18C, 19A, 19F, 22F, 23F and 33F, wherein at least serotypes 3, and 6A are conjugated to PsaA and one or more serotypes 1, 4, 5, 7F, 9V, 14, 18C, 19A, 19F, 22F, 23F and 33F are conjugated to $CRM_{197}$.

In another embodiment, the present disclosure provides a 15 valent pneumococcal vaccine comprising pneumococcal polysaccharide serotypes 1, 3, 4, 5, 6A, 6B, 7F, 9V, 14, 18C, 19A, 19F, 22F, 23F and 33F wherein at least serotypes 3, 6A and 6B are conjugated to PsaA and one or more serotypes 1, 4, 5, 7F, 9V, 14, 18C, 19A, 19F, 22F, 23F and 33F are conjugated to $CRM_{197}$.

In another embodiment, the present disclosure provides a 17 valent pneumococcal vaccine comprising pneumococcal polysaccharide serotypes 1, 3, 4, 5, 6A, 6B, 7F, 9V, 12F, 14, 18C, 19A, 19F, 22F, 23F, 33F and 35B wherein at least serotypes 3, 6A and 6B are conjugated to PsaA and one or more serotypes 1, 4, 5, 7F, 9V, 12F, 14, 18C, 19A, 19F, 22F, 23F, 33F and 35B are conjugated to $CRM_{197}$.

In another embodiment, the present disclosure provides a 20 valent pneumococcal vaccine comprising pneumococcal polysaccharide serotypes 1, 3, 4, 5, 6A, 6B, 7F, 9V, 11A, 12F, 14, 15B, 18C, 19A, 19F, 22F, 23F, 33F, 35B and 45 wherein at least serotypes 3, 6A and 6B are conjugated to PsaA and one or more serotypes 1, 4, 5, 7F, 9V, 11A, 12F, 14, 15B, 18C, 19A, 19F, 22F, 23F, 33F, 35B and 45 are conjugated to $CRM_{197}$.

In another embodiment, the present disclosure provides a 22 valent pneumococcal vaccine comprising pneumococcal polysaccharide serotypes 1, 3, 4, 5, 6A, 6B, 7F, 9V, 10A, 12F, 14, 15A, 15B, 18C, 19A, 19F, 22F, 23F, 33F, 34, 35B and 38 wherein at least serotypes 3, 6A and 6B are conjugated to PsaA and one or more serotypes 1, 4, 5, 7F, 9V, 10A, 12F, 14, 15A, 15B, 18C, 19A, 19F, 22F, 23F, 33F, 34, 35B and 38 are conjugated to $CRM_{197}$.

In another embodiment, the present disclosure provides a 22 valent pneumococcal vaccine comprising pneumococcal polysaccharide serotypes 1, 3, 4, 5, 6A, 6B, 7F, 9V, 10A, 12F, 14, 15A, 15B, 18C, 19A, 19F, 22F, 23F, 33F, 34, 35B and 38 wherein serotypes 1, 3, 6A, 10A, 12F, 15A 15B, 22F, 34, 35B, 38 are conjugated to PsaA and serotypes 14, 5, 6B, 7F, 9V, 14, 18C, 19A, 19F, 23F and 33F are conjugated to $CRM_{197}$.

In another embodiment, the present disclosure provides a 24 valent pneumococcal vaccine comprising pneumococcal polysaccharide serotypes 1, 3, 4, 5, 6A, 6B, 7F, 8, 9V, 10A, 12F, 14, 15A, 15B, 16F, 18C, 19A, 19F, 22F, 23F, 33F, 34, 35B and 38 wherein at least serotypes 3, 6A and 6B are conjugated to PsaA and one or more serotypes 1, 4, 5, 7F, 8, 9V, 10A, 12F, 14, 15A, 15B, 16F, 18C, 19A, 19F, 22F, 23F, 33F, 34, 35B and 38 are conjugated to $CRM_{197}$.

In another embodiment, the present disclosure provides a 24 valent pneumococcal vaccine comprising pneumococcal polysaccharide serotypes 1, 3, 4, 5, 6A, 6B, 7F, 8, 9V, 10A, 12F, 14, 15A, 15B, 16F 18C, 19A, 19F, 22F, 23F, 33F, 34, 35B and 38 wherein serotypes 1, 3, 6A, 8, 10A, 12F, 15A 15B, 16F 22F, 34, 35, 38 are conjugated to PsaA and one or more serotypes 14, 5, 6B, 7F, 9V, 14, 18C, 19A, 19F, 23F and 33F are conjugated to $CRM_{197}$.

In another embodiment, the present disclosure provides a 24 valent pneumococcal vaccine comprising pneumococcal polysaccharide serotypes 1, 3, 4, 5, 6A, 6B, 7F, 8, 9V, 10A, 11A, 12F, 14, 15A, 18C, 19A, 19F, 22F, 23A, 23B, 23F, 24F, 33F, 35B wherein polysaccharide from serotypes 3, 6A, 6B, 8, 10A, 11A, 12F, 15A, 23A, 23B, 24F and 35B are conjugated to PsaA and polysaccharide from serotypes 1, 4, 5, 7F, 9V, 14, 18C, 19A, 19F, 22F, 23F and 33F are conjugated to $CRM_{197}$.

In another embodiment, the present disclosure provides a 24 valent pneumococcal vaccine comprising pneumococcal polysaccharide serotypes 1, 3, 4, 5, 6A, 6B, 7F, 8, 9V, 10A, 11A, 12F, 14, 15A, 18C, 19A, 19F, 22F, 23A, 23B, 23F, 24F, 33F, 35B wherein polysaccharide from serotypes 3, 6A, 6B, 8, 10A, 11A, 12F, 15A, 23A, 23B, 24F and 35B are conjugated to PsaA and polysaccharide from serotypes 1, 4, 5, 7F, 9V, 14, 18C, 19A, 19F, 22F, 23F and 33F are conjugated to $CRM_{197}$, wherein the ratio of polysaccharide to protein (PS/protein) is about 0.3 to about 3.0.

In another embodiment, the present disclosure provides a 24 valent pneumococcal vaccine comprising pneumococcal polysaccharide serotypes 1, 3, 4, 5, 6A, 6B, 7F, 8, 9V, 10A, 11A, 12F, 14, 15A, 18C, 19A, 19F, 22F, 23A, 23B, 23F, 24F, 33F, 35B wherein polysaccharide from serotypes 3, 6A, 6B, 8, 10A, 11A, 12F, 15A, 23A, 23B, 24F and 35B are conjugated to PsaA and polysaccharide from serotypes 1, 4, 5, 7F, 9V, 14, 18C, 19A, 19F, 22F, 23F and 33F are conjugated to CRM197, wherein the Molecular weight of the each conjugate ranges from 2,000-20,000 kDa.

In another embodiment, the present disclosure provides a pneumococcal vaccine composition formulated into a dosage unit.

In another embodiment, the present disclosure provides a pneumococcal vaccine composition formulated into a dosage unit wherein the dosage unit comprises about 0.1 µg to about 50 µg of each polysaccharide, about 0.1 µg to about 10 µg, or about 1 µg to about 5 µg of each polysaccharide, wherein each polysaccharide is each individually conjugated to the carrier protein from about 1.5 µg to about 5 µg of carrier protein.

In another embodiment, the present disclosure provides a pneumococcal vaccine composition comprising a pharmaceutically acceptable diluent, buffer, preservative, stabilizer, adjuvant, and/or a lyophilization excipient.

In another embodiment, the present disclosure provides a pneumococcal vaccine composition formulated into a dosage unit that is supplied as a unit dose vial, a multiple dose vial, or a pre-filled syringe.

In another embodiment, the present disclosure provides a pneumococcal vaccine composition as a single 0.5 mL dose, the single dose comprising about 2.2 to 4.4 µg of one or more pneumococcal polysaccharides; about 1 µg to about 10 µg of PsaA conjugated to each of the one or more pneumococcal polysaccharides; about 1 µg to about 10 µg of $CRM_{197}$ conjugated to each of the one or more pneumococcal polysaccharides; about 0.2 mg to about 1 mg of aluminum phosphate adjuvant; and an excipient.

In another embodiment, the present disclosure provides a 13 valent pneumococcal vaccine comprising pneumococcal polysaccharide serotypes 1, 3, 4, 5, 6B, 7F, 9V, 14, 18C, 19A, 19F, 22F and 33F each individually conjugated to PsaA or combination of PsaA and $CRM_{197}$, wherein the pneumococcal vaccine composition is about a 0.5 mL dose formulated as a sterile liquid comprising about 2.2 µg to about 4.4 µg of each polysaccharide, about 25 µg to about 30 µg PsaA and $CRM_{197}$, about 0.125 mg of elemental aluminum as about 0.5 mg aluminum phosphate, sodium chloride, and a L-histidine buffer.

In another embodiment, the present disclosure provides a 14 valent pneumococcal vaccine comprising pneumococcal polysaccharide serotypes 1, 3, 4, 5, 6B, 7F, 9V, 14, 18C, 19A, 19F, 22F, 23F and 33F each individually conjugated to PsaA or combination of PsaA and $CRM_{197}$, wherein the pneumococcal vaccine composition is about a 0.5 mL dose formulated as a sterile liquid comprising, about 2.2 µg to about 4.4 µg of each polysaccharide, about 30 µg to about 35 µg PsaA and $CRM_{197}$, about 0.125 mg of elemental aluminum as about 0.5 mg aluminum phosphate, sodium chloride, and a L-histidine buffer.

In another embodiment, the present disclosure provides a 14 valent pneumococcal vaccine comprising pneumococcal polysaccharide serotypes 1, 3, 4, 5, 6A, 7F, 9V, 14, 18C, 19A, 19F, 22F, 23F and 33F each individually conjugated to PsaA or combination of PsaA and $CRM_{197}$, wherein the pneumococcal vaccine composition is about a 0.5 mL dose formulated as a sterile liquid comprising, about 2.2 to 4.4 µg of each polysaccharide, about 30 µg to about 35 µg PsaA and $CRM_{197}$, about 0.125 mg of elemental aluminum as about 0.5 mg aluminum phosphate, sodium chloride, and a L-histidine buffer.

In another embodiment, the present disclosure provides a 15 valent pneumococcal vaccine comprising pneumococcal polysaccharide serotypes 1, 3, 4, 5, 6A, 6B, 7F, 9V, 14, 18C, 19A, 19F, 22F, 23F and 33F wherein at least serotypes 3, 6A and 6B are conjugated to PsaA and one or more serotypes 1, 4, 5, 7F, 9V, 14, 18C, 19A, 19F, 22F, 23F and 33F are conjugated to $CRM_{197}$, wherein the pneumococcal vaccine composition is about a 0.5 mL dose formulated as a sterile liquid comprising, about 2.2 µg to about 4.4 µg of each polysaccharide, about 5 µg to about 20 µg of PsaA, about 20 µg to about 40 µg of $CRM_{197}$, about 0.125 mg of elemental aluminum as about 0.5 mg aluminum phosphate, sodium chloride, and a L-histidine buffer.

In another embodiment, the present disclosure provides a 17 valent pneumococcal vaccine comprising pneumococcal polysaccharide serotypes 1, 3, 4, 5, 6A, 6B, 7F, 9V, 12F, 14, 18C, 19A, 19F, 22F, 23F, 33F and 35B wherein at least serotypes 3, 6A and 6B are conjugated to PsaA and one or more serotypes 1, 4, 5, 7F, 9V, 12F, 14, 18C, 19A, 19F, 22F, 23F, 33F and 35B are conjugated to $CRM_{197}$, wherein the pneumococcal vaccine composition is about a 0.5 mL dose formulated as a sterile liquid comprising, about 2.2 µg to about 4.4 µg of each polysaccharide, about 5 µg to about 20 µg of PsaA, about 20 µg to about 40 µg of $CRM_{197}$, about 0.125 mg of elemental aluminum as about 0.5 mg aluminum phosphate, sodium chloride, and a L-histidine buffer.

In another embodiment, the present disclosure provides a 20 valent pneumococcal vaccine comprising pneumococcal polysaccharide serotypes 1, 3, 4, 5, 6A, 6B, 7F, 9V, 11A, 12F, 14, 15B, 18C, 19A, 19F, 22F, 23F, 33F, 35B and 45 wherein at least serotypes 3, 6A and 6B are conjugated to PsaA and one or more serotypes 1, 4, 5, 7F, 9V, 11A, 12F, 14, 15B, 18C, 19A, 19F, 22F, 23F, 33F, 35B and 45 are conjugated to $CRM_{197}$, wherein the pneumococcal vaccine composition is about a 0.5 mL dose formulated as a sterile liquid comprising, about 2.2 µg to about 4.4 µg of each polysaccharide, about 5 µg to about 20 µg of PsaA, about 20 µg to about 50 µg of $CRM_{197}$, about 0.125 mg of elemental aluminum as about 0.5 mg aluminum phosphate, sodium chloride, and a L-histidine buffer.

In another embodiment, the present disclosure provides a 22 valent pneumococcal vaccine comprising pneumococcal polysaccharide serotypes 1, 3, 4, 5, 6A, 6B, 7F, 9V, 10A, 12F, 14, 15A, 15B, 18C, 19A, 19F, 22F, 23F, 33F, 34, 35B and 38 wherein at least serotypes 3, 6A and 6B are conjugated to PsaA and one or more serotypes 1, 4, 5, 7F, 9V, 10A, 12F, 14, 15A, 15B, 18C, 19A, 19F, 22F, 23F, 33F, 34, 35B and 38 are conjugated to $CRM_{197}$, wherein the pneumococcal vaccine composition is about a 0.5 mL dose formulated as a sterile liquid comprising, about 2.2 µg to about 4.4 µg of each polysaccharide, about 5 µg to about 20 µg of PsaA, about 20 µg to about 50 µg of $CRM_197$, about 0.125 mg of elemental aluminum as about 0.5 mg aluminum phosphate, sodium chloride, and a L-histidine buffer.

In another embodiment, the present disclosure provides a 22 valent pneumococcal vaccine comprising pneumococcal polysaccharide serotypes 1, 3, 4, 5, 6A, 6B, 7F, 9V, 10A, 12F, 14, 15A, 15B, 18C, 19A, 19F, 22F, 23F, 33F, 34, 35B and 38 wherein serotypes 1, 3, 6A, 10A, 12F, 15A 15B, 22F, 34, 35B, 38 are conjugated to PsaA and serotypes 14, 5, 6B, 7F, 9V, 14, 18C, 19A, 19F, 23F and 33F are conjugated to CRM$_{197}$, wherein the pneumococcal vaccine composition is about a 0.5 mL dose formulated as a sterile liquid comprising, about 2.2 µg to about 4.4 µg of each polysaccharide, about 20 µg to about 40 µg of PsaA, about 20 µg to about 40 µg of CRM$_{197}$, about 0.125 mg of elemental aluminum as about 0.5 mg aluminum phosphate, sodium chloride, and a L-histidine buffer.

In another embodiment, the present disclosure provides a 24 valent pneumococcal vaccine comprising pneumococcal polysaccharide serotypes 1, 3, 4, 5, 6A, 6B, 7F, 8, 9V, 10A, 12F, 14, 15A, 15B, 16F, 18C, 19A, 19F, 22F, 23F, 33F, 34, 35B and 38 wherein at least serotypes 3, 6A and 6B are conjugated to PsaA and one or more serotypes 1, 4, 5, 7F, 8, 9V, 10A, 12F, 14, 15A, 15B, 16F, 18C, 19A, 19F, 22F, 23F, 33F, 34, 35B and 38 are conjugated to CRM$_{197}$, wherein the pneumococcal vaccine composition is about a 0.5 mL dose formulated as a sterile liquid comprising, about 2.2 µg to about 4.4 µg of each polysaccharide, about 5 µg to about 20 µg of PsaA, about 20 µg to about 50 µg of CRM$_{197}$, about 0.125 mg of elemental aluminum as about 0.5 mg aluminum phosphate, sodium chloride, and a L-histidine buffer.

In another embodiment, the present disclosure provides a 24 valent pneumococcal vaccine comprising pneumococcal polysaccharide serotypes 1, 3, 4, 5, 6A, 6B, 7F, 8, 9V, 10A, 11A, 12F, 14, 15A, 18C, 19A, 19F, 22F, 23A, 23B, 23F, 24F, 33F, 35B wherein polysaccharide from serotypes 3, 6A, 6B, 8, 10A, 11A, 12F, 15A, 23A, 23B, 24F and 35B are conjugated to PsaA and polysaccharide from serotypes 1, 4, 5, 7F, 9V, 14, 18C, 19A, 19F, 22F, 23F and 33F are conjugated to CRM$_{197}$, wherein the pneumococcal vaccine composition is about a 0.5 mL dose formulated as a sterile liquid comprising, about 2.2 µg to about 4.4 µg of each polysaccharide, about 20 µg to about 24 µg of PsaA, about 20 µg to about 30 µg of CRM$_{197}$, about 0.125 mg of elemental aluminum as about 0.5 mg aluminum phosphate, sodium chloride.

DETAILED DESCRIPTION

Figure 1:
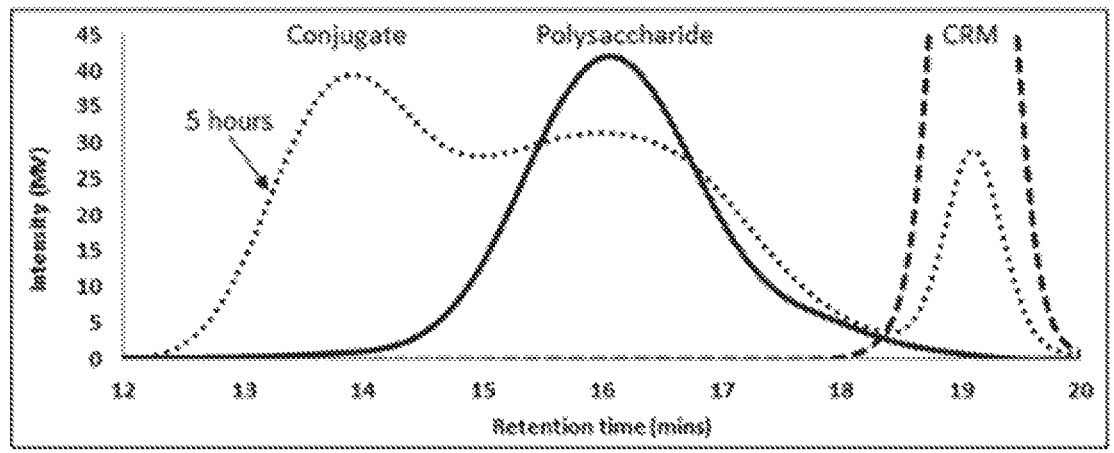
FIG. 1: An SEC-HPLC chromatogram illustrates conjugation reaction kinetics of serotype 7F (A), serotype 14 (B), serotype 19F (C), serotype 3 (D), serotype 6A (E), and serotype 6B (F).
Figure 1:
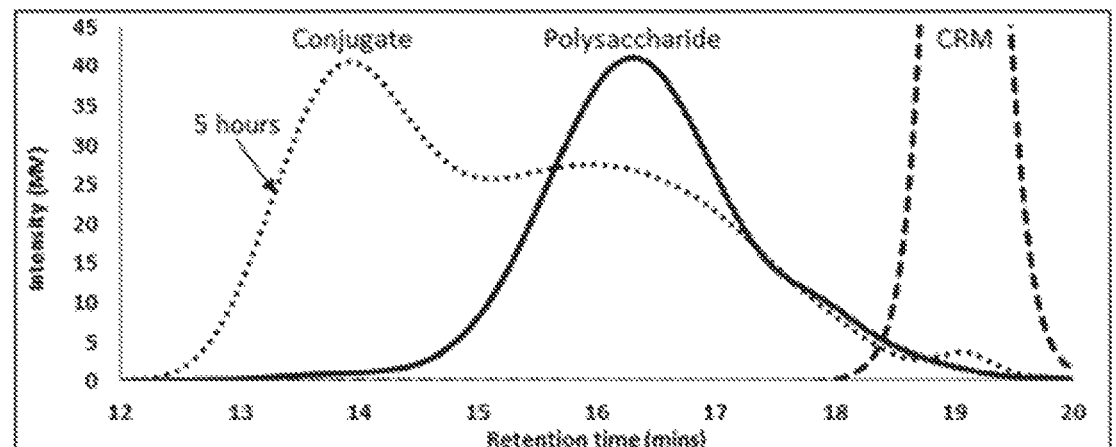
Figure 1:
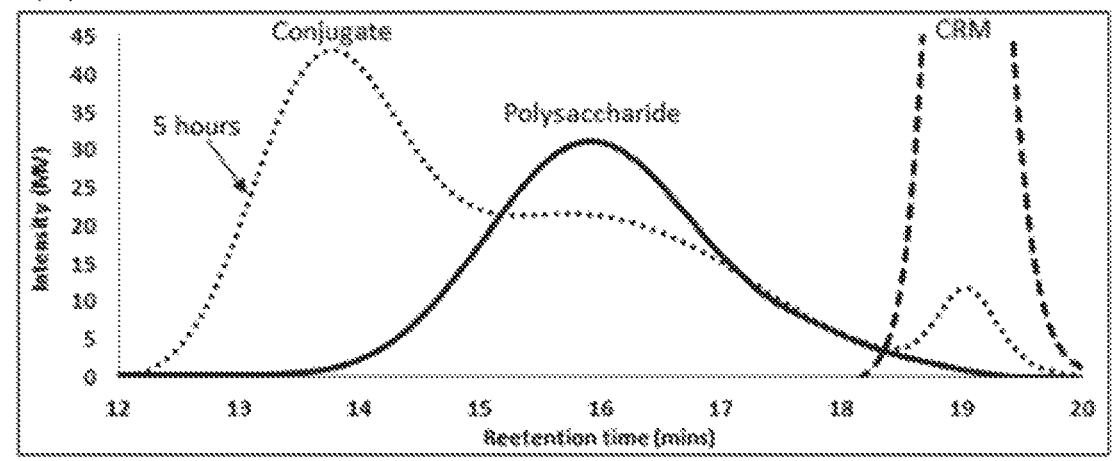

In an embodiment, the present disclosure provides a pneumococcal vaccine composition comprising pneumococcal polysaccharides where one or more of the pneumococcal polysaccharides are native pneumococcal polysaccharides.

In another embodiment, the present disclosure provides a pneumococcal vaccine composition comprising pneumococcal polysaccharides where one or more of the pneumococcal polysaccharides are fragmented, each fragmented pneumococcal polysaccharide having an average molecular weight less than that of a native pneumococcal polysaccharide.

In another embodiment, the present disclosure provides a pneumococcal vaccine composition comprising pneumococcal polysaccharides where each of the pneumococcal polysaccharides is activated with 1-cyano-4-dimethyl-amino-pyridinium tetrafluoroborate (CDAP) to form a cyanate ester prior to conjugation to the carrier protein.

In another embodiment, the present disclosure provides a pneumococcal vaccine composition comprising pneumococcal polysaccharides where one or more of the pneumococcal polysaccharides are directly coupled to an amino group of the carrier protein or are coupled to the amino group by a spacer.

In another embodiment, the present disclosure provides a pneumococcal vaccine composition comprising pneumococcal polysaccharides wherein the spacer is cystamine, cysteamine, hexane diamine, adipic acid dihydrazide (ADH), EDAC or EDC.

In another embodiment, the present disclosure provides a pneumococcal vaccine composition comprising pneumococcal polysaccharides of one or more serotypes and a carrier protein wherein the PsaA carrier protein is a modified PsaA and does not include wild-type hydrophobic N-terminal leader peptide.

In another embodiment, the present disclosure provides a pneumococcal vaccine composition comprising pneumococcal polysaccharides of one or more serotypes and a carrier protein wherein the PsaA carrier protein includes 290 amino acids.

The present disclosure provides a pneumococcal vaccine composition comprising two or more capsular pneumococcal polysaccharide serotypes each individually conjugated to a carrier protein, referred to herein as polysaccharide-protein conjugates and/or conjugates. When included in the pneumococcal vaccine composition described herein, pneumococcal vaccine is a multivalent pneumococcal polysaccharide-protein conjugate vaccine (also referred to herein as multivalent conjugate vaccine, conjugate vaccine, and/or polysaccharide-protein conjugate vaccine). In addition to the multivalent conjugate vaccine, the present disclosure provides a process for preparing and/or administering the same to a subject in need thereof.

In some embodiments, the pneumococcal vaccine composition is a multivalent immunogenic composition comprising one or more conjugates. For example, the conjugates may include two or more pneumococcal polysaccharides, each of the pneumococcal polysaccharides selected from pneumococcal polysaccharides of serotypes 1, 2, 3, 4, 5, 6A, 6B, 6C, 7F, 8, 9N, 9V, 10A, 11A, 12F, 14, 15A, 15B, 15C, 16F, 17F, 18C, 19F, 19A, 20A, 20B, 22F, 23A, 23B, 23F, 24B, 24F, 31, 33F, 34, 35B, 35F, 38, 39, and 45.

In some embodiments, the pneumococcal vaccine composition is multivalent and comprises five pneumococcal polysaccharides (5 valent), ten pneumococcal polysaccharides (10 valent), eleven pneumococcal polysaccharides (11 valent), twelve pneumococcal polysaccharides (12 valent), thirteen pneumococcal polysaccharides (13 valent), fourteen pneumococcal polysaccharides (14 valent), fifteen pneumococcal polysaccharides (15 valent), sixteen pneumococcal polysaccharides (16 valent), seventeen pneumococcal polysaccharides (17 valent), eighteen pneumococcal polysaccharides (18 valent), nineteen pneumococcal polysaccharides (19 valent), twenty pneumococcal polysaccharides (20 valent), twenty-one pneumococcal polysaccharides (21 valent), twenty-two pneumococcal polysaccharides (22 valent), twenty-three pneumococcal polysaccharides (23 valent), twenty-four pneumococcal polysaccharides (24 valent), twenty-five pneumococcal polysaccharides (25 valent), twenty-six pneumococcal polysaccharides (26 valent), twenty-seven pneumococcal polysaccharides (27 valent), twenty-eight pneumococcal polysaccharides (28 valent), twenty-nine pneumococcal polysaccharides (29 valent), or thirty pneumococcal polysaccharides (30 valent). In other embodiments, the pneumococcal vaccine composition is a 10 valent, 14 valent, 15 valent, 17 valent, 18 valent, 19 valent, 20 valent, 22 valent, 23 valent, 24 valent or 25 valent pneumococcal vaccine composition.

Surprisingly, the multivalent pneumococcal conjugate vaccine compositions of the present disclosure offer an improved immune response compared to multivalent pneumococcal vaccines comprising pneumococcal polysaccharides not conjugated to carrier proteins. More specifically, the multivalent pneumococcal conjugate vaccine compositions of the present disclosure were surprisingly most effective when the pneumococcal polysaccharides from one or more serotypes of Streptococcus pneumoniae are conjugated to PsaA and/or $CRM_{197}$.

Carrier proteins are non-toxic and non-reactogenic proteins that are obtainable in a sufficient amount and purity. In some embodiments, the present disclosure provides a pneumococcal conjugate vaccine composition comprising one or more carrier proteins conjugated to one or more S. pneumoniae polysaccharides (also referred to herein as "pneumococcal polysaccharides"). By conjugating a pneumococcal polysaccharide to a carrier protein, the pneumococcal polysaccharide has increased immunogenicity compared to an unconjugated pneumococcal polysaccharide. Carrier proteins useful with the present disclosure should be amenable to standard conjugation procedures.

$CRM_{197}$ is a variant of diphtheria toxin and is non-toxic for use in vaccines. $CRM_{197}$ may be isolated from cultures of Corynebacterium diphtheriae strain C7 (β197) grown in casamino acids and yeast extract-based medium. $CRM_{197}$ may be prepared recombinantly in accordance with the methods described in U.S. Pat. No. 5,614,382. Alternatively, $CRM_{197}$ may be prepared recombinantly in accordance with the methods known in the literature or according to the method disclosed in PCT publication WO 2016/079755. $CRM_{197}$ may be purified by ultrafiltration, ammonium sulphate precipitation, and ion-exchange chromatography or other methods well known in art.

In some embodiments, the pneumococcal polysaccharides of the present disclosure are conjugated to one or more carrier proteins. For example, a pneumococcal polysaccharide is each individually conjugated to a carrier protein. In other embodiments, more than one pneumococcal polysaccharide is conjugated to a carrier protein. For example, two pneumococcal polysaccharides, three pneumococcal polysaccharides, four pneumococcal polysaccharides, five pneumococcal polysaccharides, six pneumococcal polysaccharides, seven pneumococcal polysaccharides, eight pneumococcal polysaccharides, nine pneumococcal polysaccharides, or ten pneumococcal polysaccharides are conjugated to a carrier protein. In some embodiments, a pneumococcal polysaccharide is conjugated to more than one carrier protein. For example, a pneumococcal polysaccharide is conjugated to one carrier protein, two carrier proteins, three carrier proteins, and/or four carrier proteins.

In some embodiments, the carrier protein is PsaA. In additional embodiments, a combination of the carrier protein used, which includes two or more carrier proteins, such as PsaA and $CRM_{197}$ which are each individually conjugated to each pneumococcal polysaccharide. In further embodiments, the carrier protein is two carrier proteins and includes PsaA and $CRM_{197}$.

In some embodiments, the carrier protein is selected from one or more of the following carrier proteins, PsaA, $CRM_{197}$, inactivated bacterial toxins such as tetanus toxoid, pertussis toxoid; cholera toxoid, exotoxin A from Pseudomonas aeruginosa, bacterial outer membrane proteins such as outer membrane complex c (OMPC), porins, transferrin binding proteins, pneumolysin, PspA, C5a peptidase from Group A or Group B streptococcus, or Haemophilus influenzae protein D, ovalbumin, keyhole limpet hemocyanin, (KLH), bovine serum albumin (BSA) and purified protein derivative of tuberculin (PPD).

Furthermore, one or more of the conjugates may include native (e.g., wild-type) carrier proteins and/or one or more of the conjugates may include carrier proteins modified from their native form to a non-native form (e.g., engineered to lack one or more amino acids). In some embodiments, carrier proteins may be engineered to eliminate one or more protein domains, such as a leader peptide, or other domains that might have properties which are undesirable for conjugates of the present disclosure. For example, PsaA may be a 290 amino acid carrier protein engineered to lack a hydrophobic N-terminal leader peptide having hydropathy index of 2.052.

In some embodiments, the present disclosure provides a pneumococcal polysaccharide-protein conjugate vaccine composition comprising pneumococcal polysaccharides (e.g., capsular pneumococcal polysaccharides) selected from serotypes 1, 2, 3, 4, 5, 6A, 6B, 6C, 7F, 8, 9N, 9V, 10A, 11A, 12F, 14, 15A, 15B, 15C, 16F, 17F, 18C, 19F, 19A, 20A, 20B, 22F, 23A, 23B, 23F, 24B, 24F, 31, 33F, 34, 35B, 35F, 38, 39 and 45. The selected pneumococcal polysaccharides are each individually conjugated to carrier protein PsaA or a first portion of the selected pneumococcal polysaccharides are conjugated to PsaA and a second portion of the selected pneumococcal polysaccharides are conjugated to $CRM_{197}$. In any of these embodiments, the pneumococcal polysaccharide-protein conjugate vaccine composition is an immunogenic multivalent pneumococcal polysaccharide-protein conjugate composition, such as a 10 valent, 13 valent, 14 valent, 15 valent, 17 valent, 18 valent, 19 valent, 20 valent, 22 valent, 23 valent, 24 valent or 25 valent immunogenic multivalent pneumococcal polysaccharide-protein conjugate composition.

In some embodiments, the present disclosure provides a pneumococcal polysaccharide-protein conjugate vaccine composition comprising pneumococcal polysaccharides (e.g., capsular pneumococcal polysaccharides) selected from serotypes 1, 2, 3, 4, 5, 6A, 6B, 6C, 7F, 8, 9N, 9V, 10A, 11A, 12F, 14, 15A, 15B, 15C, 16F, 17F, 18C, 19F, 19A, 20A, 20B, 22F, 23A, 23B, 23F, 24B, 24F, 31, 33F, 34, 35B, 35F, 38, 39 and 45. The selected pneumococcal polysaccharides are each individually conjugated to carrier protein PsaA. In other embodiments, a first portion of the selected pneumococcal polysaccharides are conjugated to PsaA and a second portion of the selected pneumococcal polysaccharides are conjugated to $CRM_{197}$. In any of these embodiments, the pneumococcal polysaccharide-protein conjugate vaccine composition is an immunogenic multivalent pneumococcal polysaccharide-protein conjugate composition, such as a 10 valent, 13 valent, 14 valent, 15 valent, 17 valent, 18 valent, 19 valent, 20 valent, 22 valent, 23 valent, 24 valent or 25 valent immunogenic multivalent pneumococcal polysaccharide-protein conjugate composition.

In further embodiments, the present disclosure provides a pneumococcal polysaccharide-protein conjugate vaccine composition comprising pneumococcal polysaccharides (e.g., capsular pneumococcal polysaccharides) selected from serotypes 1, 2, 3, 4, 5, 6A, 6B, 6C, 7F, 8, 9N, 9V, 10A, 11A, 12F, 14, 15A, 15B, 15C, 16F, 17F, 18C, 19F, 19A, 20A, 20B, 22F, 23A, 23B, 23F, 24B, 24F, 31, 33F, 34, 35B, 35F, 38, 39 and 45. In these embodiments, at least three of the selected pneumococcal polysaccharides are each individually conjugated to carrier protein PsaA and additional pneumococcal polysaccharides are each individually conjugated to carrier protein $CRM_{197}$. In any of these embodiments, the pneumococcal polysaccharide-protein conjugate vaccine composition is an immunogenic multivalent pneumococcal polysaccharide-protein conjugate composition, such as a 10 valent, 13 valent, 14 valent, 15 valent, 17 valent, 18 valent, 19 valent, 20 valent, 22 valent, 23 valent, 24 valent or 25 valent immunogenic multivalent pneumococcal polysaccharide-protein conjugate composition.

In further embodiments, the present disclosure provides a pneumococcal polysaccharide-protein conjugate vaccine composition comprising pneumococcal polysaccharides (e.g., capsular pneumococcal polysaccharides) selected from serotypes 1, 2, 3, 4, 5, 6A, 6B, 6C, 7F, 8, 9N, 9V, 10A, 11A, 12F, 14, 15A, 15B, 15C, 16F, 17F, 18C, 19F, 19A, 20A, 20B, 22F, 23A, 23B, 23F, 24B, 24F, 31, 33F, 34, 35B, 35F, 38, 39 and 45. In these embodiments, at least a first five of the selected pneumococcal polysaccharides are each individually conjugated to carrier protein PsaA and at least a second five polysaccharides are each individually conjugated to carrier protein $CRM_{197}$. The first five selected pneumococcal polysaccharides are selected from serotypes 1, 2, 3, 4, 5, 6A, 6B, 6C, 7F, 8, 9N, 9V, 10A, 11A, 12F, 14, 15A, 15B, 15C, 16F, 17F, 18C, 19F, 19A, 20A, 20B, 22F, 23A, 23B, 23F, 24B, 24F, 31, 33F, 34, 35B, 35F, 38, 39 and 45 and the second five selected from serotypes 1, 2, 3, 4, 5, 6A, 6B, 6C, 7F, 8, 9N, 9V, 10A, 11A, 12F, 14, 15A, 15B, 15C, 16F, 17F, 18C, 19F, 19A, 20A, 20B, 22F, 23A, 23B, 23F, 24B, 24F, 31, 33F, 34, 35B, 35F, 38, 39 and 45. In other embodiments, a first portion of the selected pneumococcal polysaccharides are conjugated to PsaA and a second portion of the selected pneumococcal polysaccharides are conjugated to $CRM_{197}$. In any of these embodiments, the pneumococcal polysaccharide-protein conjugate vaccine composition is an immunogenic multivalent pneumococcal polysaccharide-protein conjugate composition, such as a 10 valent, 14 valent, 15 valent, 17 valent, 18 valent, 19 valent, 20 valent, 22 valent, 23 valent, 24 valent or 25 valent immunogenic multivalent pneumococcal polysaccharide-protein conjugate composition.

In further embodiments, the present disclosure provides a 14 valent pneumococcal polysaccharide-protein conjugate vaccine composition comprising at least three pneumococcal polysaccharides (e.g., capsular pneumococcal polysaccharides) selected from serotypes 1, 2, 3, 4, 5, 6A, 6B, 6C, 7F, 8, 9N, 9V, 10A, 11A, 12F, 14, 15A, 15B, 15C, 16F, 17F, 18C, 19F, 19A, 20A, 20B, 22F, 23A, 23B, 23F, 24B, 24F, 31, 33F, 34, 35B, 35F, 38, 39 and 45, and are conjugated to PsaA. Moreover, the 14 valent pneumococcal polysaccharide-protein conjugate vaccine composition further comprises at least five pneumococcal polysaccharides selected from serotypes 1, 2, 3, 4, 5, 6A, 6B, 6C, 7F, 8, 9N, 9V, 10A, 11A, 12F, 14, 15A, 15B, 15C, 16F, 17F, 18C, 19F, 19A, 20A, 20B, 22F, 23A, 23B, 23F, 24B, 24F, 31, 33F, 34, 35B, 35F, 38, 39 and 45, and are conjugated to $CRM_{197}$.

In further embodiments, the present disclosure provides a 15 valent pneumococcal polysaccharide-protein conjugate vaccine composition comprising at least three pneumococcal polysaccharides (e.g., capsular pneumococcal polysaccharides) selected from serotypes 1, 2, 3, 4, 5, 6A, 6B, 6C, 7F, 8, 9N, 9V, 10A, 11A, 12F, 14, 15A, 15B, 15C, 16F, 17F, 18C, 19F, 19A, 20A, 20B, 22F, 23A, 23B, 23F, 24B, 24F, 31, 33F, 34, 35B, 35F, 38, 39 and 45, and are conjugated to PsaA. Moreover, the 15 valent pneumococcal polysaccharide-protein conjugate vaccine composition further comprises at least five pneumococcal polysaccharides selected from serotypes 1, 2, 3, 4, 5, 6A, 6B, 6C, 7F, 8, 9N, 9V, 10A, 11A, 12F, 14, 15A, 15B, 15C, 16F, 17F, 18C, 19F, 19A, 20A, 20B, 22F, 23A, 23B, 23F, 24B, 24F, 31, 33F, 34, 35B, 35F, 38, 39 and 45, and are conjugated to $CRM_{197}$.

In some embodiments, the present disclosure provides a 17 valent pneumococcal polysaccharide-protein conjugate vaccine composition comprising at least three pneumococcal polysaccharides (e.g., capsular pneumococcal polysaccharides) selected from serotypes 1, 2, 3, 4, 5, 6A, 6B, 6C, 7F, 8, 9N, 9V, 10A, 11A, 12F, 14, 15A, 15B, 15C, 16F, 17F, 18C, 19F, 19A, 20A, 20B, 22F, 23A, 23B, 23F, 24B, 24F, 31, 33F, 34, 35B, 35F, 38, 39 and 45, and are conjugated to PsaA. Moreover, the 17 valent pneumococcal polysaccharide-protein conjugate vaccine composition further comprises at least five pneumococcal polysaccharides selected from serotypes 1, 2, 3, 4, 5, 6A, 6B, 6C, 7F, 8, 9N, 9V, 10A, 11A, 12F, 14, 15A, 15B, 15C, 16F, 17F, 18C, 19F, 19A, 20A, 20B, 22F, 23A, 23B, 23F, 24B, 24F, 31, 33F, 34, 35B, 35F, 38, 39 and 45, and are conjugated to $CRM_{197}$.

In other embodiments, the present disclosure provides a 20 valent pneumococcal polysaccharide-protein conjugate vaccine composition comprising at least three pneumococcal polysaccharides (e.g., capsular pneumococcal polysaccharides) selected from serotypes 1, 2, 3, 4, 5, 6A, 6B, 6C, 7F, 8, 9N, 9V, 10A, 11A, 12F, 14, 15A, 15B, 15C, 16F, 17F, 18C, 19F, 19A, 20A, 20B, 22F, 23A, 23B, 23F, 24B, 24F, 31, 33F, 34, 35B, 35F, 38, 39 and 45, and are conjugated to PsaA. Moreover, the 20 valent pneumococcal polysaccharide-protein conjugate vaccine composition further comprises at least five pneumococcal polysaccharides selected from serotypes 1, 2, 3, 4, 5, 6A, 6B, 6C, 7F, 8, 9N, 9V, 10A, 11A, 12F, 14, 15A, 15B, 15C, 16F, 17F, 18C, 19F, 19A, 20A, 20B, 22F, 23A, 23B, 23F, 24B, 24F, 31, 33F, 34, 35B, 35F, 38, 39 and 45, and are conjugated to $CRM_{197}$.

In additional embodiments, the present disclosure provides a 22 valent pneumococcal polysaccharide-protein conjugate vaccine composition comprising at least five pneumococcal polysaccharides (e.g., capsular pneumococcal polysaccharides) selected from serotypes 1, 2, 3, 4, 5, 6A, 6B, 6C, 7F, 8, 9N, 9V, 10A, 11A, 12F, 14, 15A, 15B, 15C, 16F, 17F, 18C, 19F, 19A, 20A, 20B, 22F, 23A, 23B, 23F, 24B, 24F, 31, 33F, 34, 35B, 35F, 38, 39 and 45, and are conjugated to PsaA. Moreover, the 22 valent pneumococcal polysaccharide-protein conjugate vaccine composition further comprises at least five pneumococcal polysaccharides selected from serotypes 1, 2, 3, 4, 5, 6A, 6B, 6C, 7F, 8, 9N, 9V, 10A, 11A, 12F, 14, 15A, 15B, 15C, 16F, 17F, 18C, 19F, 19A, 20A, 20B, 22F, 23A, 23B, 23F, 24B, 24F, 31, 33F, 34, 35B, 35F, 38, 39 and 45, and are conjugated to $CRM_{197}$.

In some embodiments, the present disclosure provides a 24 valent pneumococcal polysaccharide-protein conjugate vaccine composition comprising at least five pneumococcal polysaccharides (e.g., capsular pneumococcal polysaccharides) selected from serotypes 1, 2, 3, 4, 5, 6A, 6B, 6C, 7F, 8, 9N, 9V, 10A, 11A, 12F, 14, 15A, 15B, 15C, 16F, 17F, 18C, 19F, 19A, 20A, 20B, 22F, 23A, 23B, 23F, 24B, 24F, 31, 33F, 34, 35B, 35F, 38, 39 and 45, and are conjugated to PsaA. Moreover, the 24 valent pneumococcal polysaccharide-protein conjugate vaccine composition further comprises at least five pneumococcal polysaccharides selected from serotypes 1, 2, 3, 4, 5, 6A, 6B, 6C, 7F, 8, 9N, 9V, 10A, 11A, 12F, 14, 15A, 15B, 15C, 16F, 17F, 18C, 19F, 19A, 20A, 20B, 22F, 23A, 23B, 23F, 24B, 24F, 31, 33F, 34, 35B, 35F, 38, 39 and 45, and are conjugated to $CRM_{197}$.

In further embodiments, the present disclosure provides a 25 valent pneumococcal polysaccharide-protein conjugate vaccine composition comprising at least five pneumococcal polysaccharides (e.g., capsular pneumococcal polysaccharides) selected from serotypes 1, 2, 3, 4, 5, 6A, 6B, 6C, 7F, 8, 9N, 9V, 10A, 11A, 12F, 14, 15A, 15B, 15C, 16F, 17F, 18C, 19F, 19A, 20A, 20B, 22F, 23A, 23B, 23F, 24B, 24F, 31, 33F, 34, 35B, 35F, 38, 39 and 45, and are conjugated to PsaA. Moreover, the 25 valent pneumococcal polysaccharide-protein conjugate vaccine composition further comprises at least five pneumococcal polysaccharides selected from serotypes 1, 2, 3, 4, 5, 6A, 6B, 6C, 7F, 8, 9N, 9V, 10A, 11A, 12F, 14, 15A, 15B, 15C, 16F, 17F, 18C, 19F, 19A, 20A, 20B, 22F, 23A, 23B, 23F, 24B, 24F, 31, 33F, 34, 35B, 35F, 38, 39 and 45, and are conjugated to $CRM_{197}$.

In other embodiments, the present disclosure provides a 14 valent pneumococcal polysaccharide-protein conjugate vaccine composition comprising pneumococcal polysaccharides (e.g., capsular pneumococcal polysaccharides) selected from serotypes 1, 3, 4, 5, 6B, 7F, 9V, 14, 18C, 19A, 19F, 22F, 23F and 33F. Of the selected serotypes, at least serotype 3, and serotype 6B are conjugated to PsaA, and each of one or more serotypes 1, 4, 5, 7F, 9V, 14, 18C, 19A, 19F, 22F, 23F and 33F are conjugated to $CRM_{197}$.

In other embodiments, the present disclosure provides a 14 valent pneumococcal polysaccharide-protein conjugate vaccine composition comprising pneumococcal polysaccharides (e.g., capsular pneumococcal polysaccharides) selected from serotypes 1, 3, 4, 5, 6A, 7F, 9V, 14, 18C, 19A, 19F, 22F, 23F and 33F. Of the selected serotypes, at least serotype 3, and serotype 6A are conjugated to PsaA, and each of one or more serotypes 1, 4, 5, 7F, 9V, 14, 18C, 19A, 19F, 22F, 23F and 33F are conjugated to $CRM_{197}$.

In additional embodiments, the present disclosure provides a 15 valent pneumococcal polysaccharide-protein conjugate vaccine composition comprising pneumococcal polysaccharides (e.g., capsular pneumococcal polysaccharides) selected from serotypes 1, 3, 4, 5, 6A, 6B, 7F, 9V, 14, 18C, 19A, 19F, 22F, 23F and 33F. Of the selected serotypes, at least serotypes 3, 6A, and 6B are conjugated to PsaA, and each of one or more serotypes 1, 4, 5, 7F, 9V, 14, 18C, 19A, 19F, 22F, 23F and 33F are conjugated to $CRM_{197}$.

In some embodiments, the present disclosure provides a 17 valent pneumococcal polysaccharide-protein conjugate vaccine composition comprising pneumococcal polysaccharides (e.g., capsular pneumococcal polysaccharides) selected from serotypes 1, 3, 4, 5, 6A, 6B, 7F, 9V, 12F, 14, 18C, 19A, 19F, 22F, 23F, 33F and 35B. Of the selected serotypes, at least serotypes 3, 6A, and 6B are conjugated to PsaA, and each of one or more serotypes 1, 4, 5, 7F, 9V, 12F, 14, 18C, 19A, 19F, 22F, 23F, 33F and 35B are conjugated to $CRM_{197}$.

In some embodiments, the present disclosure provides a 20 valent pneumococcal polysaccharide-protein conjugate vaccine composition comprising pneumococcal polysaccharides (e.g., capsular pneumococcal polysaccharides) selected from serotypes 1, 3, 4, 5, 6A, 6B, 7F, 9V, 11A, 12F, 14, 15B, 18C, 19A, 19F, 22F, 23F, 33F, 35B and 45. Of the selected serotypes, at least serotypes 3, 6A, and 6B are conjugated to PsaA, and each of one or more serotypes 1, 4, 5, 7F, 9V, 11A, 12F, 14, 15B, 18C, 19A, 19F, 22F, 23F, 33F, 35B and 45 are conjugated to $CRM_{197}$.

In other embodiments, the present disclosure provides a 22 valent pneumococcal polysaccharide-protein conjugate vaccine composition comprising pneumococcal polysaccharides (e.g., capsular pneumococcal polysaccharides) selected from serotypes 1, 3, 4, 5, 6A, 6B, 7F, 9V, 10A, 12F, 14, 15A, 15B, 18C, 19A, 19F, 22F, 23F, 33F, 34, 35B and 38. Of the selected serotypes, at least serotypes 3, 6A, and 6B are conjugated to PsaA, and each of one or more serotypes 1, 4, 5, 7F, 9V, 10A, 12F, 14, 15A, 15B, 18C, 19A, 19F, 22F, 23F, 33F, 34, 35B and 38 are conjugated to $CRM_{197}$.

In other embodiments, the present disclosure provides a 22 valent pneumococcal polysaccharide-protein conjugate vaccine composition comprising pneumococcal polysaccharides (e.g., capsular pneumococcal polysaccharides) selected from serotypes 1, 3, 4, 5, 6A, 6B, 7F, 9V, 10A, 12F, 14, 15A, 15B, 18C, 19A, 19F, 22F, 23F, 33F, 34, 35B and 38. Of the selected serotypes, serotypes 1, 3, 6A, 10A, 12F, 15A 15B, 22F, 34, 35, and 38 are conjugated to PsaA, and each of serotypes 14, 5, 6B, 7F, 9V, 14, 18C, 19A, 19F, 23F and 33F are conjugated to $CRM_{197}$.

In other embodiments, the present disclosure provides a 24 valent pneumococcal polysaccharide-protein conjugate vaccine composition comprising pneumococcal polysaccharides (e.g., capsular pneumococcal polysaccharides) selected from serotypes 1, 3, 4, 5, 6A, 6B, 7F, 8, 9V, 10A, 12F, 14, 15A, 15B, 16F, 18C, 19A, 19F, 22F, 23F, 33F, 34, 35B and 38. Of the selected serotypes, serotypes 1, 3, 6A, 8, 10A, 12F, 15A 15B, 16F, 22F, 34, 35, and 38 are conjugated to PsaA, and each of serotypes 14, 5, 6B, 7F, 9V, 14, 18C, 19A, 19F, 23F and 33F are conjugated to $CRM_{197}$.

The pneumococcal polysaccharide-protein conjugate compositions of the present disclosure further comprise one or more of the following: a pharmaceutically acceptable carrier, a pharmaceutically acceptable diluent, a buffer, a preservative, a stabilizer, an adjuvant, and/or a lyophilization excipient. For example, the pneumococcal polysaccharide-protein conjugate compositions of the present disclosure may comprise a pharmaceutically acceptable carrier. In some embodiments, the pneumococcal polysaccharide-protein conjugate compositions of the present disclosure comprise at least 10 pneumococcal polysaccharides selected from serotypes 1, 2, 3, 4, 5, 6A, 6B, 6C, 7F, 8, 9N, 9V, 10A, 11A, 12F, 14, 15A, 15B, 15C, 16F, 17F, 18C, 19F, 19A, 20A, 20B, 22F, 23A, 23B, 23F, 24B, 24F, 31, 33F, 34, 35B, 35F, 38, 39 and 45. The selected serotypes are each individually conjugated to PsaA or a combination of PsaA and $CRM_{197}$, and a pharmaceutically acceptable carrier.

In some embodiments, the pneumococcal polysaccharides useful in the compositions of the present disclosure may be extracted from one or more microorganisms (e.g. *Streptococcus pneumoniae*) according to conventional methods. For example, pneumococcal polysaccharides may be prepared according to known procedures. Furthermore, purification of the pneumococcal polysaccharides may be performed according to the procedure described in PCT publication WO 2016/174683 A1.

The extracted pneumococcal polysaccharides may be purified according to conventional methods and may be used in its native form. In other embodiments, the extracted and purified pneumococcal polysaccharides may be fragmented to obtain one or more portions of the pneumococcal polysaccharide, each portion of the pneumococcal polysaccharide having an average molecular weight less than that of the extracted and purified pneumococcal polysaccharides.

In another embodiment, the present disclosure provides a pneumococcal vaccine composition comprising pneumococcal polysaccharides, each pneumococcal polysaccharide having a molecular between about 150 kDa and 450 kDa.

In another embodiment, the present disclosure provides a pneumococcal vaccine composition comprising one or more capsular pneumococcal polysaccharide serotype each individually conjugated to a carrier protein, such as a polysaccharide-protein conjugate wherein each polysaccharide-protein conjugate has a molecular weight of about 1,500 kDa to about 15,000 kDa.

In other embodiments, the extracted and purified pneumococcal polysaccharides may be activated prior to conjugation to one or more carrier proteins. For example, the extracted and purified pneumococcal polysaccharides may be activated (e.g., chemically) prior to conjugation to one or more carrier proteins. Each activated pneumococcal polysaccharide may be each individually conjugated to a carrier protein forming a polysaccharide-protein conjugate (e.g., a glycoconjugate). In other embodiments, one or more of the activated pneumococcal polysaccharides may be conjugated to an individual carrier protein and/or an activated pneumococcal polysaccharide may be conjugated to an individual carrier protein. The conjugates may be prepared by known techniques.

In some embodiments, the pneumococcal polysaccharides may be chemically activated and subsequently conjugated to carrier proteins according to known techniques, such as those described in U.S. Pat. Nos. 4,365,170, 4,673,574 and 4,902,506. For example, pneumococcal polysaccharides can be activated by oxidation of a terminal hydroxyl group to an aldehyde with an oxidizing agent, such as periodate (e.g., sodium periodate, potassium periodate, or periodic acid) by random oxidative cleavage of one or more vicinal hydroxyl groups of the carbohydrates and formation of one or more reactive aldehyde groups.

The pneumococcal polysaccharides may also be activated by CDAP (1-cyano-4-dimethylamino-pyridinium tetrafluoroborate) and subsequently conjugated to one or more carrier proteins such as PsaA, $CRM_{197}$, PspA, or combination thereof. In other embodiments, pneumococcal polysaccharides activated with CDAP to form a cyanate ester may be directly conjugated to one or more carrier proteins or conjugated using a spacer (e.g., linker). The spacer may couple to an amino group on the carrier protein. In some embodiments, the spacer may be cystamine or cysteamine, which generates a thiolated polysaccharide that may be coupled to the carrier protein through a thioether linkage to a maleimide-activated carrier protein (e.g., using GMBS) or a haloacetylated carrier protein (e.g., using iodoacetimide, ethyl iodoacetimide HCl, SIAB, SIA, SBAP, and/or N-succinimidyl bromoacetate. In other embodiments, the cyanate ester is coupled using hexane diamine or adipic acid dihydrazide (ADH) and an amino-derivatized saccharide is conjugated to a carrier protein using carbodiimide (e.g. EDAC or EDC) chemistry via a carboxyl group on the protein carrier. Such conjugates are described in International Patent Application Publication No. WO 93/15760, International Patent Application Publication No. WO 95/08348, International Patent Application Publication No. WO 96/29094, and Chu et al., 1983, Infect. Immunity 40:245-256.

Other suitable activation and/or coupling techniques for use with the polysaccharide-protein conjugates and vaccine compositions of the present disclosure include use of carbodiimides, hydrazides, active esters, norborane, p-nitrobenzoic acid, N-hydroxysuccinimide, S—NHS, EDC, TSTU, and other methods described in International Patent Application Publication No. WO 98/42721. For example, conjugation may involve a carbonyl linker which may be formed by reaction of a free hydroxyl group of the saccharide with CDI (See Bethell et al., 1979, J. Biol. Chem. 254:2572-4; Heam et al., 1981, J. Chromatogr. 218:509-18) followed by coupling with a protein to form a carbamate linkage. In some embodiments, the anomeric terminus may be reduced to a primary hydroxyl group, optional protection/deprotection of the primary hydroxyl group, reaction of the primary hydroxyl group with CDI to form a CDI carbamate intermediate and coupling the CDI carbamate intermediate with an amino group on a protein.

For example, another suitable activation and/or coupling techniques for use with the polysaccharide-protein conjugates and vaccine compositions of the present disclosure include the following method: sized pneumococcal polysaccharides (e.g., about 6 mL of sized polysaccharide at a concentration of about 10 mg/mL) and CDAP (e.g., about 100 mg/mL in acetonitrile (w/v)) can be mixed in a glass vial in a ratio of about 1 to about 1 (e.g., by stirring for about 1 minute). The pH of the polysaccharide solution may be adjusted as necessary (e.g., to about 9.25 with about 0.2M triethylamine and stirred for 3 min at room temperature). In addition, PsaA (e.g., about 4 mL of a solution having a concentration of about 15 mg/mL) may be added slowly to the activated pneumococcal polysaccharides (e.g., in a ratio of about 1 to about 1 (Ps:Carrier protein)). The pH of the reaction may be adjusted (e.g., to about 9.05 using 0.2M trimethylamine) and the reaction may be continued (e.g., by stirring for 5 hours at room temperature). The reaction mixture may be quenched (e.g., by addition of an excess concentration of glycine).

In some embodiments, the reaction mixture may be diafiltered using a membrane (e.g., a 100 K MWCO membrane) and may be purified by size-exclusion chromatography. The diafiltered and purified fractions may be analyzed using SEC-MALLS, and an anthrone method. The analyzed fractions containing conjugates may be pooled and sterile filtered (e.g., using 0.2 µm filters).

Following conjugation of pneumococcal polysaccharides to one or more carrier proteins, the polysaccharide-protein conjugates may be purified (e.g., enriched with respect to the amount of polysaccharide-protein conjugate) by a variety of techniques. These techniques include, but are not limited to concentration/diafiltration operations, precipitation/elution, column chromatography, and depth filtration. For example, after the conjugates are purified, the conjugates may be compounded to formulate the pneumococcal polysaccharide-protein conjugate compositions of the present disclosure, which may be used as vaccines.

In some embodiments, the present disclosure provides a method for preparing a polysaccharide-protein conjugate of the pneumococcal vaccine composition described herein wherein the method further comprises formulating the polysaccharide-protein conjugate into the pneumococcal vaccine composition including an adjuvant, an excipient, and a buffer.

In some embodiments, the present disclosure provides a method for preparing a polysaccharide-protein conjugate of the pneumococcal vaccine composition described herein wherein the adjuvant is aluminum phosphate.

In some embodiments, the present disclosure provides a method of treating a subject in need thereof comprising, administering a pneumococcal vaccine composition described herein to the subject in need thereof.

In some embodiments, the subject has a disease mediated by Streptococcus pneumoniae, such as invasive pneumococcal disease (IPD).

In one embodiment, the subject is a human, such as an infant (less than about 1 year of age), a toddler (about 12 months to about 24 months of age), a young child (about 2 years to about 5 years of age), an older child (about 5 years to about 13 years of age), an adolescent (about 13 years to about 18 years of age), an adult (about 18 years to about 65 years of age), or an elder (more than about 65 years of age).

In some embodiments, the present disclosure provides a method of inducing an immune response to an S. pneumoniae capsular polysaccharide conjugate comprising administering an immunologically effective amount of the pneumococcal vaccine composition described herein to a subject.

In one embodiment, method of inducing an immune response to an S. pneumoniae capsular polysaccharide conjugate, comprising administering the pneumococcal vaccine composition described herein to the subject systemically, subcutaneously, and/or mucousally.

In some embodiments, an amount of each conjugate in a dose of the vaccine compositions of the present disclosure is an amount sufficient to induce an immunoprotective response, such as an immunoprotective response without significant, adverse effects. While the amount of each conjugate may vary depending upon the pneumococcal serotype, each dose of the vaccine compositions may comprise about 0.1 µg to about 50 µg of each pneumococcal polysaccharide, about 0.1 µg to about 10 µg, or about 1 µg to about 5 µg of each pneumococcal polysaccharide conjugated to each carrier protein comprising about 1.5 µg to about 5 µg of carrier protein.

In another embodiment, the present disclosure provides a pneumococcal vaccine composition comprising pneumococcal polysaccharides and carrier proteins, the pneumococcal vaccine composition having a percent ratio of protein to polysaccharide (protein/PS) of about 0.5 to about 2.0 protein/PS, preferably, 0.7 to 1.2.

In some embodiments, the present disclosure provides pneumococcal polysaccharide-protein conjugate vaccine compositions comprising pneumococcal polysaccharides having molecular weights ranging between about 100 kDa to about 400 kDa, about 125 kDa to about 425 kDa, about 150 kDa to about 450 kDa, about 175 kDa to about 475 kDa, about 200 kDa to about 500 kDa, about 250 kDa to about 550 kDa, or about 300 kDa to about 600 kDa.

In other embodiments, the present disclosure provides pneumococcal polysaccharide-protein conjugate vaccine compositions comprising one or more polysaccharide-protein conjugates having a molecular weight ranging between about 1,000 kDa to about 10,000 kDa, about 1,500 kDa to about 15,000 kDa, about 2,000 kDa to about 20,000 kDa, about 2,500 kDa to about 25,000 kDa, or about 3,000 kDa to about 30,000 kDa.

The pneumococcal polysaccharide-protein conjugate vaccine compositions of the present disclosure may be manufactured using known methods. For example, the pneumococcal polysaccharide-protein conjugate vaccine compositions may be formulated with a pharmaceutically acceptable diluent or vehicle, e.g. water or a saline solution. In addition, the pneumococcal polysaccharide-protein conjugate vaccine compositions may further include one or more of the following: a buffer, a preservative or a stabilizer, polysorbate, an adjuvant such as an aluminum compound, e.g. an aluminium hydroxide, an aluminium phosphate or an aluminium hydroxyphosphate, and/or a lyophilization excipient. Inclusion of any one of the above compounds in the pneumococcal polysaccharide-protein conjugate vaccine compositions of the present disclosure may be selected as a function of the mode and route of administration to a subject in need thereof and may further be based on standard pharmaceutical practices.

In some embodiments, the present disclosure provides a method for preparing a fourteen valent pneumococcal polysaccharide-protein conjugate composition comprising pneumococcal polysaccharides selected from serotypes 1, 3, 4, 5, 6B, 7F, 9V, 14, 18C, 19A, 19F, 22F, 23F and 33F, wherein at least serotypes 3, and 6B are conjugated to PsaA and one or more serotypes 1, 4, 5, 7F, 9V, 14, 18C, 19A, 19F, 22F, 23F and 33F are conjugated to $CRM_{197}$. The method for preparing the fourteen valent pneumococcal polysaccharide-protein conjugate composition comprises the steps of;
(a) individually conjugating one or more of the fourteen pneumococcal polysaccharides (e.g., activated utilizing CDAP) to an immunogenic carrier protein, such as PsaA and/or $CRM_{197}$,
(b) diafiltering and purifying the conjugates using size exclusion chromatography,
(c) analyzing the purified fractions using SEC-MALLS, pooling fractions containing each of the fourteen conjugates, and filter sterilizing the monovalent conjugate fractions, and
(d) formulating the fourteen conjugates (e.g., about 2.2 to 4.4 µg for each serotype, about 5 µg to about 10 µg of PsaA, and about 15 µg to about 36 µg of $CRM_{197}$), an adjuvant (such as aluminum phosphate), an excipient, and buffer into the fourteen valent pneumococcal polysaccharide-protein conjugate composition.

In some embodiments, the fourteen valent pneumococcal polysaccharide-protein conjugate composition may be filtered (e.g., aseptically).

In some embodiments, the present disclosure provides a method for preparing a fourteen valent pneumococcal polysaccharide-protein conjugate composition comprising pneumococcal polysaccharides selected from serotypes 1, 3, 4, 5, 6A, 7F, 9V, 14, 18C, 19A, 19F, 22F, 23F and 33F, wherein at least serotypes 3, and 6A are conjugated to PsaA and one or more serotypes 1, 4, 5, 7F, 9V, 14, 18C, 19A, 19F, 22F, 23F and 33F are conjugated to $CRM_{197}$. The method for preparing the fourteen valent pneumococcal polysaccharide-protein conjugate composition comprises the steps of;
(a) individually conjugating one or more of the fourteen pneumococcal polysaccharides (e.g., activated utilizing CDAP) to an immunogenic carrier protein, such as PsaA and/or $CRM_{197}$,
(b) diafiltering and purifying the conjugates using size exclusion chromatography,
(c) analyzing the purified fractions using SEC-MALLS, pooling fractions containing each of the fourteen conjugates, and filter sterilizing the monovalent conjugate fractions, and (d) formulating the fourteen conjugates (e.g., about 2.2 to 4.4 µg for each serotype, about 5 µg to about 10 µg of PsaA, and about 15 µg to about 36 µg of $CRM_{197}$), an adjuvant (such as aluminum phosphate), an excipient, and buffer into the fourteen valent pneumococcal polysaccharide-protein conjugate composition.

In some embodiments, the fourteen valent pneumococcal polysaccharide-protein conjugate composition may be filtered (e.g., aseptically).

In some embodiments, the present disclosure provides a method for preparing a fifteen valent pneumococcal polysaccharide-protein conjugate composition comprising pneumococcal polysaccharides selected from serotypes 1, 3, 4, 5, 6A, 6B, 7F, 9V, 14, 18C, 19A, 19F, 22F, 23F and 33F wherein at least serotypes 3, 6A and 6B are conjugated to PsaA and one or more serotypes 1, 4, 5, 7F, 9V, 14, 18C, 19A, 19F, 22F, 23F and 33F are conjugated to $CRM_{197}$. The method for preparing the fifteen valent pneumococcal polysaccharide-protein conjugate composition comprises the steps of;
  (a) individually conjugating one or more of the fifteen pneumococcal polysaccharides (e.g., activated utilizing CDAP) to an immunogenic carrier protein, such as PsaA and/or $CRM_{197}$.
  (b) diafiltering and purifying the conjugates using size exclusion chromatography.
  (c) analyzing the purified fractions using SEC-MALLS, pooling fractions containing each of the fifteen conjugates, and filter sterilizing the monovalent conjugate fractions, and
  (d) formulating the fifteen conjugates (e.g., about 2.2 to 4.4 µg for each serotype, about 5 µg to about 20 µg of PsaA, and about 20 µg to about 40 µg of $CRM_{19}7$), an adjuvant (such as aluminum phosphate), an excipient, and buffer into the fifteen valent pneumococcal polysaccharide-protein conjugate composition.

In some embodiments, the fifteen valent pneumococcal polysaccharide-protein conjugate composition may be filtered (e.g., aseptically).

In some embodiments, the present disclosure provides a method for preparing a seventeen valent pneumococcal polysaccharide-protein conjugate composition comprising pneumococcal polysaccharides selected from serotypes 1, 3, 4, 5, 6A, 6B, 7F, 9V, 12F, 14, 18C, 19A, 19F, 22F, 23F, 33F and 35B wherein at least serotypes 3, 6A and 6B are conjugated to PsaA and one or more serotypes 1, 4, 5, 7F, 9V, 12F, 14, 18C, 19A, 19F, 22F, 23F, 33F and 35B are conjugated to $CRM_{197}$. The method for preparing the seventeen valent pneumococcal polysaccharide-protein conjugate composition comprises the steps of;
  (a) individually conjugating one or more of the seventeen pneumococcal polysaccharides (e.g., activated utilizing CDAP) to an immunogenic carrier protein, such as PsaA and/or $CRM_{197}$,
  (b) diafiltering and purifying the conjugates using size exclusion chromatography,
  (c) analyzing the purified fractions using SEC-MALLS, pooling fractions containing each of the seventeen conjugates, and filter sterilizing the monovalent conjugate fractions, and
  (d) formulating the seventeen conjugates (e.g., about 2.2 to 4.4 µg for each serotype, about 5 µg to about 20 µg of PsaA, and about 20 µg to about 40 µg of $CRM_{197}$), an adjuvant (such as aluminum phosphate), an excipient, and buffer into the seventeen valent pneumococcal polysaccharide-protein conjugate composition.

In some embodiments, the seventeen valent pneumococcal polysaccharide-protein conjugate composition may be filtered (e.g., aseptically).

In some embodiments, the present disclosure provides a method for preparing a twenty valent pneumococcal polysaccharide-protein conjugate composition comprising pneumococcal polysaccharides selected from serotypes 1, 3, 4, 5, 6A, 6B, 7F, 9V, 11A, 12F, 14, 15B, 18C, 19A, 19F, 22F, 23F, 33F, 35B and 45 wherein at least serotypes 3, 6A and 6B are conjugated to PsaA and one or more serotypes 1, 4, 5, 7F, 9V, 11A, 12F, 14, 15B, 18C, 19A, 19F, 22F, 23F, 33F, 35B and 45 are conjugated to $CRM_{197}$. The method for preparing the twenty valent pneumococcal polysaccharide-protein conjugate composition comprises the steps of;
  (a) individually conjugating one or more of the twenty pneumococcal polysaccharides (e.g., activated utilizing CDAP) to an immunogenic carrier protein, such as PsaA and/or $CRM_{197}$,
  (b) diafiltering and purifying the conjugates using size exclusion chromatography,
  (c) analyzing the purified fractions using SEC-MALLS, pooling fractions containing each of the twenty conjugates, and filter sterilizing the monovalent conjugate fractions, and
  (d) formulating the twenty conjugates (e.g., about 2.2 to 4.4 µg for each serotype, about 5 µg to about 20 µg of PsaA, and about 20 µg to about 50 µg of $CRM_{197}$), an adjuvant (such as aluminum phosphate), an excipient, and buffer into the twenty valent pneumococcal polysaccharide-protein conjugate composition.

In some embodiments, the twenty valent pneumococcal polysaccharide-protein conjugate composition may be filtered (e.g., aseptically).

In some embodiments, the present disclosure provides a method for preparing a twenty-two valent pneumococcal polysaccharide-protein conjugate composition comprising one or more pneumococcal polysaccharides selected from serotypes 1, 3, 4, 5, 6A, 6B, 7F, 9V, 10A, 12F, 14, 15A, 15B, 18C, 19A, 19F, 22F, 23F, 33F, 34, 35B and 38 wherein at least serotypes 3, 6A and 6B are conjugated to PsaA and one or more serotypes 1, 4, 5, 7F, 9V, 10A, 12F, 14, 15A, 15B, 18C, 19A, 19F, 22F, 23F, 33F, 34, 35B and 38 are conjugated to $CRM_{197}$. The method for preparing the twenty-two valent pneumococcal polysaccharide-protein conjugate composition comprises the steps of;
  (a) individually conjugating one or more of the twenty-two pneumococcal polysaccharides (e.g., activated utilizing CDAP) to an immunogenic carrier protein, such as PsaA and/or $CRM_{197}$,
  (b) diafiltering and purifying the conjugates using size exclusion chromatography,
  (c) analyzing the purified fractions using SEC-MALLS, pooling fractions containing each of the twenty-two conjugates, and filter sterilizing the monovalent conjugate fractions, and
  (d) formulating the twenty-two conjugates (e.g., about 2.2 to 4.4 µg for each serotype, about 5 µg to about 20 µg of PsaA, and about 20 µg to about 50 µg of $CRM_{197}$), an adjuvant (such as aluminum phosphate), an excipient, and buffer into the twenty-two valent pneumococcal polysaccharide-protein conjugate composition.

In some embodiments, the twenty-two valent pneumococcal polysaccharide-protein conjugate composition may be filtered (e.g., aseptically).

The compositions of the present disclosure may be formulated into a unit dose, for example, a unit dose vial, into a multiple dose, for example, a multiple dose vial, or a pre-filled syringe. The compositions of the present disclosure may further comprise of one or more preservative(s) selected from thiomersal, 2-phenoxyethanol and the like, in an amount which may range from about 4 mg/mL to about 20 mg/mL.

In some embodiments, the present disclosure also provides an immunogenic composition (e.g., a vaccine), such as a pneumococcal polysaccharide-protein conjugate composition, administered as a single dose of about 0.5 mL formulated to contain at least the following: about 2.2 to 4.4 µg of two or more pneumococcal polysaccharide serotypes, about 1 µg to about 10 µg of PsaA per serotype, about 1 µg to about 10 µg of $CRM_{197}$ for each serotype, about 0.2 mg to about 1 mg of an adjuvant (e.g., aluminum phosphate), and one or more excipients (e.g., sodium chloride, and/or a buffer).

In other embodiments, the present disclosure also provides a thirteen valent immunogenic composition (e.g., a vaccine) in a sterile liquid formulation, such as a thirteen valent pneumococcal polysaccharide-protein conjugate composition, administered as a single dose of about 0.5 mL formulated to contain at least the following: pneumococcal polysaccharide serotypes 1, 3, 4, 5, 6B, 7F, 9V, 14, 18C, 19A, 19F, 22F and 33F each individually conjugated to PsaA or combination of PsaA and $CRM_{197}$.

The thirteen valent vaccine may be further formulated into one or more doses of about 0.5 mL dose, each 0.5 mL dose comprising about 2.2 µg to about 4.4 µg of each of the thirteen serotypes, about 25 µg to about 30 µg PsaA and $CRM_{197}$, about 0.125 mg of an adjuvant (e.g., elemental aluminum such as about 0.5 mg aluminum phosphate), sodium chloride, and L-histidine buffer.

In some embodiments, the present disclosure also provides a fourteen valent immunogenic composition (e.g., a vaccine) in a sterile liquid formulation, such as a fourteen valent pneumococcal polysaccharide-protein conjugate composition, administered as a single dose of about 0.5 mL formulated to contain at least the following: pneumococcal polysaccharide serotypes 1, 3, 4, 5, 6B, 7F, 9V, 14, 18C, 19A, 19F, 22F, 23F and 33F each individually conjugated to PsaA or combination of PsaA and $CRM_{197}$.

In some embodiments, the present disclosure also provides a fourteen valent immunogenic composition (e.g., a vaccine) in a sterile liquid formulation, such as a fourteen valent pneumococcal polysaccharide-protein conjugate composition, administered as a single dose of about 0.5 mL formulated to contain at least the following: pneumococcal polysaccharide serotypes 1, 3, 4, 5, 6A, 7F, 9V, 14, 18C, 19A, 19F, 22F, 23F and 33F each individually conjugated to PsaA or combination of PsaA and $CRM_{197}$.

The fourteen valent vaccine may be further formulated into one or more doses of about 0.5 mL dose, each 0.5 mL dose comprising about 2.2 µg to about 4.4 µg of each of the fourteen serotypes, about 20 µg to about 35 µg PsaA and $CRM_{197}$, about 0.125 mg of an adjuvant (e.g., elemental aluminum such as about 0.5 mg aluminum phosphate), sodium chloride, and L-histidine buffer.

In other embodiments, the present disclosure also provides a fifteen valent immunogenic composition (e.g., a vaccine) in a sterile liquid formulation, such as a fifteen valent pneumococcal polysaccharide-protein conjugate composition, administered as a single dose of about 0.5 mL formulated to contain at least the following: pneumococcal polysaccharide serotypes 1, 3, 4, 5, 6A, 6B, 7F, 9V, 14, 18C, 19A, 19F, 22F, 23F and 33F, wherein at least serotypes 3, 6A and 6B are each individually conjugated to PsaA and one or more serotypes 1, 4, 5, 7F, 9V, 14, 18C, 19A, 19F, 22F, 23F and 33F are each individually conjugated to $CRM_{197}$.

The fifteen valent vaccine may be further formulated into one or more doses of about 0.5 mL dose, each 0.5 mL dose comprising about 2.2 µg to about 4.4 µg of each of the fifteen serotypes, about 5 µg to about 20 µg PsaA, about 20 µg to 40 µg of $CRM_{197}$, about 0.125 mg of an adjuvant (e.g., elemental aluminum such as about 0.5 mg aluminum phosphate), sodium chloride, and L-histidine buffer.

In additional embodiments, the present disclosure also provides a seventeen valent immunogenic composition (e.g., a vaccine) in a sterile liquid formulation, such as a seventeen valent pneumococcal polysaccharide-protein conjugate composition, administered as a single dose of about 0.5 mL formulated to contain at least the following: pneumococcal polysaccharide serotypes 1, 3, 4, 5, 6A, 6B, 7F, 9V, 12F, 14, 18C, 19A, 19F, 22F, 23F, 33F and 35B, wherein at least serotypes 3, 6A and 6B are each individually conjugated to PsaA and one or more serotypes 1, 4, 5, 7F, 9V, 12F, 14, 18C, 19A, 19F, 22F, 23F, 33F and 35B are each individually conjugated to $CRM_{197}$.

The seventeen valent vaccine may be further formulated into one or more doses of about 0.5 mL dose, each 0.5 mL dose comprising about 2.2 µg to about 4.4 µg of each of the seventeen serotypes, about 5 µg to about 20 µg PsaA, about 20 µg to 40 µg of $CRM_{197}$, about 0.125 mg of an adjuvant (e.g., elemental aluminum such as about 0.5 mg aluminum phosphate), sodium chloride, and L-histidine buffer.

In some embodiments, the present disclosure also provides a twenty valent immunogenic composition (e.g., a vaccine) in a sterile liquid formulation, such as a twenty valent pneumococcal polysaccharide-protein conjugate composition, administered as a single dose of about 0.5 mL formulated to contain at least the following: pneumococcal polysaccharide serotypes 1, 3, 4, 5, 6A, 6B, 7F, 9V, 11A, 12F, 14, 15B, 18C, 19A, 19F, 22F, 23F, 33F, 35B and 45, wherein at least serotypes 3, 6A and 6B are each individually conjugated to PsaA and one ore more serotypes 1, 4, 5, 7F, 9V, 11A, 12F, 14, 15B, 18C, 19A, 19F, 22F, 23F, 33F, 35B and 45 are each individually conjugated to $CRM_{197}$.

The twenty valent vaccine may be further formulated into one or more doses of about 0.5 mL dose, each 0.5 mL dose comprising about 2.2 µg to about 4.4 µg of each of the twenty serotypes, about 5 µg to about 20 µg PsaA, about 20 µg to 50 µg of $CRM_{197}$, about 0.125 mg of an adjuvant (e.g., elemental aluminum such as about 0.5 mg aluminum phosphate), sodium chloride, and L-histidine buffer.

In some embodiments, the present disclosure also provides a twenty-two valent immunogenic composition (e.g., a vaccine) in a sterile liquid formulation, such as a twenty-two valent pneumococcal polysaccharide-protein conjugate composition, administered as a single dose of about 0.5 mL formulated to contain at least the following: pneumococcal polysaccharide serotypes 1, 3, 4, 5, 6A, 6B, 7F, 9V, 10A, 12F, 14, 15A, 15B, 18C, 19A, 19F, 22F, 23F, 33F, 34, 35B and 38, wherein at least serotypes 3, 6A and 6B are each individually conjugated to PsaA and one or more serotypes 1, 4, 5, 7F, 9V, 10A, 12F, 14, 15A, 15B, 18C, 19A, 19F, 22F, 23F, 33F, 34, 35B and 38 are each individually conjugated to $CRM_{197}$.

The twenty-two valent vaccine may be further formulated into one or more doses of about 0.5 mL dose, each 0.5 mL dose comprising about 2.2 µg to about 4.4 µg of each of the twenty-two serotypes, about 5 µg to about 20 µg PsaA, about 20 µg to 50 µg of $CRM_{197}$, about 0.125 mg of an adjuvant (e.g., elemental aluminum such as about 0.5 mg aluminum phosphate), sodium chloride, and L-histidine buffer.

In some embodiments, the present disclosure also provides a twenty-four valent immunogenic composition (e.g., a vaccine) in a sterile liquid formulation, such as a twenty-four valent pneumococcal polysaccharide-protein conjugate composition, administered as a single dose of about 0.5 mL formulated to contain at least the following: pneumococcal polysaccharide serotypes 1, 3, 4, 5, 6A, 6B, 7F, 8, 9V, 10A, 12F, 14, 15A, 15B, 16F, 18C, 19A, 19F, 22F, 23F, 33F, 34, 35B and 38, wherein at least serotypes 3, 6A and 6B are each individually conjugated to PsaA and one or more serotypes 1, 4, 5, 7F, 8, 9V, 10A, 12F, 14, 15A, 15B, 16F, 18C, 19A, 19F, 22F, 23F, 33F, 34, 35B and 38 are each individually conjugated to $CRM_{197}$.

The twenty-four valent vaccine may be further formulated into one or more doses of about 0.5 mL dose, each 0.5 mL dose comprising about 2.2 µg to about 4.4 µg of each of the twenty-two serotypes, about 5 µg to about 20 µg PsaA, about 20 µg to 50 µg of $CRM_{197}$, about 0.125 mg of an adjuvant (e.g., elemental aluminum such as about 0.5 mg aluminum phosphate), sodium chloride, and L-histidine buffer.

Compositions of the present disclosure may be administered to a subject in need thereof by any number of conventional routes used in the field of vaccines. For example, compositions of the present disclosure may be administered systemically, such as parenterally (e.g. subcutaneously, intramuscularly, intradermally and/or intravenously) or mucosally (e.g., orally and/or nasally).

In some embodiments, the present disclosure also provides methods of inducing an immune response in a subject in need thereof to one or more S. pneumoniae capsular polysaccharides conjugated to one or more carrier proteins. The methods for inducing the immune response comprise administering an immunologically effective amount of the compositions described herein to the subject in need thereof.

According to the methods of the present disclosure, the subject to whom the compositions described herein is a human, such as an infant (less than about 1 year of age), a toddler (about 12 months to about 24 months of age), a young child (about 2 years to about 5 years of age), an older child (about 5 years to about 13 years of age), an adolescent (about 13 years to about 18 years of age), an adult (about 18 years to about 65 years of age), or an elder (more than about 65 years of age).

As used herein, an "effective amount" of the compositions described in the present disclosure refers to an amount required to elicit an immune response in the subject to which the composition was administered. The immune response is characterized by the presence of one or more S. pneumoniae antigen-specific antibodies in the host that significantly reduce the likelihood or severity of infection of S. pneumoniae during a subsequent challenge.

Capsular saccharides from S. pneumoniae serotypes of the present disclosure may be produced by process known in the art which involves growing each S. pneumoniae serotype in a medium; lysing the cells at the end of the growth cycle and harvesting the lysate broth for downstream process. Purification of each polysaccharide is carried out following the procedure disclosed in WO 2016/174683A1.

EXAMPLES

The following examples are provided to illustrate the disclosure and are merely for illustrative purpose only and should not be construed to limit the scope of the disclosure.

Example 1: Conjugation of Individual Pneumococcal Polysaccharide to Carrier Protein to Form Polysaccharide-PsaA Conjugates A) PsaA Preparation:

The PsaA gene was PCR amplified from *Streptococcus pneumoniae* Serotype 4, without its hydrophobic leader peptide sequence. The gene was sequence verified and cloned into *E. coli* using a vector constructed in-house (pBE66) for higher expression.

Glycerol stock culture encoding the PSaA gene was revived on a 20 mL LB Media containing 1 mL of Glycerol Stock in a 150 mL conical flask. The culture was incubated for about 6 hrs at 37° C. under 200 rpm to a final $OD_{600\ nm}$ of 3.5 OD. The revived culture was transferred to 1 L seed culture in a 5 L conical flask. The culture was grown for about 10 hrs at 37° C. under 200 rpm to a final OD 600 nm of 3.

The seed culture was transferred aseptically to a 20 L fermenter containing the following media components. HyPeptone 6 g/L, Yeast extract 12/L, di Potassium Hydrogen ortho phosphate 13.5 g/L, ammonium phosphate di basic 4 g/L, Citric acid 1.7 g/L, $MgSO_4.7H_2O$ 1.2 g/L, Glucose 4 g/L, thamine HCL 10 mg/L along with 1 mL/L trace elements (e.g., trace elements for 100 mL composition $FeCl_3$ 2.7 g, $ZnCl_2$ 0.2 g, $CoCl_2.6H_2O$ 0.2 g, $Na_2MoO_4.2H_2O$ 0.2 g, $CuSO_4$ $5H_2O$ 0.1 g, Boric Acid 0.05 g, $CaCl_2$ $2H_2O$ 0.1 g, Conc., HCL 10 mL.) The initial fermentation started with $OD_{600\ nm}$ 0.2 OD. The pH was maintained at 7±0.2 throughout the fermentation with 20% ortho-phosphoric acid and 12.5% ammonium hydroxide.

When the glucose level falls below 0.5 g/L the feed batch was initiated at a steady rate of 3-4 g/L/hr, the DO % was maintained>20% throughout the fermentation with oxygen enrichment.

Cells were grown in the fermentor and the cell pellet was harvested by centrifugation. The cells were lysed using cell-disruption device (Panda). The lysate was centrifuged at 10000 g, the clarified supernatant was subject to purification.

PsaA purification was performed similar to the procedure described in Larentis et. al, 2011 (Protein expression and Purification 78 (2011) 38). Purification was further optimized by using mixed mode chromatography (Ceramic Hydroxyapatite Type-II) after DEAE to achieve higher purity of PsaA.

Anion Exchange Chromatography:

30 mL of DEAE Sepharose (GE) resin was packed in XK16/20 column. The resin was washed with 5 column volumes of sterile distilled water followed by 10 column volumes of 20 mM Tris, 1 mM EDTA, pH 8.0 (Equilibration buffer). 30 mL of supernatant was diluted to 100 mL with equilibration buffer and loaded onto column and flow through was collected. The column was washed with 5 volumes of equilibration buffer. PsaA was eluted with 12 volumes of linear gradient of (0-100% B). (Buffer A containing 20 mM Tris, 1 mM EDTA pH 8.0; Buffer B-20 mM Tris, 1 mM EDTA, 250 mM NaCl pH 8.0.) This was followed by washing the columns with 20 mM Tris, 1 mM EDTA, 1 M NaCl pH8.0.

Mixed Mode Chromatography:

25 ml of Ceramic Hydroxyapatite Type II (CHT-II) was packed in column. The resin was washed with volumes of sterile distilled water followed by 10 volumes of 20 mM Tris pH 6.8. Elution fractions from DEAE resin that showed clear major visible band of approximately 37 KD good concentration of PsaA on SDS PAGE were pooled and loaded onto CHT-II resin. The flow through was collected and the column was washed with 5 column volumes of equilibration buffer. Protein was eluted with 5 column volumes step gradients of (15% B, 20% B, 50% B and 100% B). Buffer A contains 20 mM Tris pH 6.8, while the Buffer B contains 250 mM Phosphate buffer pH 6.8.

All the elution fractions showing a clean band at the expected size of PsaA were pooled, concentrated by 10 kDa MWCO cassette and diafiltered against 20 mM Phosphate buffer pH 7.5. The purified protein was loaded on SDS-PAGE gel to assess purity.

B) Activation and Conjugation of Pneumococcal Polysaccharide Serotype 3 to PsaA

The size reduced polysaccharide of serotype 3 (concentration of 5 mg/mL) and 1.5 mL of CDAP (100 mg/mL in acetonitrile (w/v)) was mixed in a glass bottle in the ratio of 1:0.5 (PS:CDAP) and stirred for 1 min. The pH of the polysaccharide solution was adjusted to 9.0 with 3.5 mL of 0.2M triethylamine and stirred for 1 min at room temperature (RT). 210 mg of PsaA (14.0 mL of 15.0 mg/mL concentration) was added slowly to the activated polysaccharide in a ratio of 1:0.7 (Ps:Carrier protein).

The pH of the reaction was adjusted to about 9.01 with 0.7 mL of 0.2M triethylamine and the reaction was continued under stirring for 5 hours at room temperature followed by quenching of the reaction by adding excess concentration of glycine (100 mM). The conjugation kinetics of reactions were monitored using SEC-HPLC at each hour of the reaction.

The reaction mixture was diafiltered and concentrated using 100 kDa MWCO TFF membrane. Concentrate was purified by size-exclusion chromatography. The fractions were analyzed by SEC-MALLS, anthrone method and fractions containing conjugates were pooled and sterile filtered with 0.2 μm filters.

C) Activation and Conjugation of Pneumococcal Polysaccharide Serotype 6A to PsaA The size reduced polysaccharide Type 6A (concentration of 14.6 mg/mL) and 400 μL of CDAP (100 mg/mL in Acetonitrile (w/v)) was mixed in a glass bottle in the ratio of 1:1 (PS:CDAP) and stirred for 1 min. The pH of the polysaccharide solution was adjusted to 9.5 with 800 μL of 0.2M triethylamine and stirred for 1 min at room temperature (RT). 40 mg of PsaA (3.78 mL of 11.0 mg/mL concentration) was added slowly to the activated polysaccharide in a ratio of 1:1 (Ps:Carrier protein).

The pH of the reaction was adjusted to about 9.01 with 0.7 mL of 0.2M triethylamine and the reaction was continued under stirring for 5 hours at room temperature followed by quenching of the reaction by adding excess concentration of glycine (100 mM). The conjugation kinetics of reactions were monitored using SEC-HPLC at each hour of the reaction.

The reaction mixture was diafiltered and concentrated using 100 kDa MWCO TFF membrane. Concentrate was purified by size-exclusion chromatography. The fractions were analyzed by SEC-MALLS, anthrone method and fractions containing conjugates were pooled and sterile filtered with 0.2 μm filters.

D) Activation and Conjugation of Pneumococcal Polysaccharide Serotype 6B to PsaA The size reduced polysaccharide Type 6B (concentration of 14.97 mg/mL) and 4.0 mL of CDAP (100 mg/mL in acetonitrile (w/v)) was mixed in a glass bottle in the ratio of 1:2 (PS:CDAP) and stirred for 1 min. The pH of the polysaccharide solution was adjusted to 9.1 with 8.0 mL of 0.2M Triethylamine and stirred for 1 min at room temperature (RT). 340 mg of PsaA (22.66 mL of 15.0 mg/mL concentration) was added slowly to the activated polysaccharide in a ratio of 1:1.7 (Ps:Carrier protein).

The pH of the reaction was adjusted to about 9.01 with 0.7 mL of 0.2M triethylamine and the reaction was continued under stirring for 5 hours at room temperature followed by quenching of the reaction by adding excess concentration of glycine (100 mM). The conjugation kinetics of reactions were monitored using SEC-HPLC at each hour of the reaction.

The reaction mixture was diafiltered and concentrated using 100 kDa MWCO TFF membrane. Concentrate was purified by size-exclusion chromatography. The fractions were analyzed by SEC-MALLS, anthrone method and fractions containing conjugates were pooled and sterile filtered with 0.2 μm filters.

Figure 2:
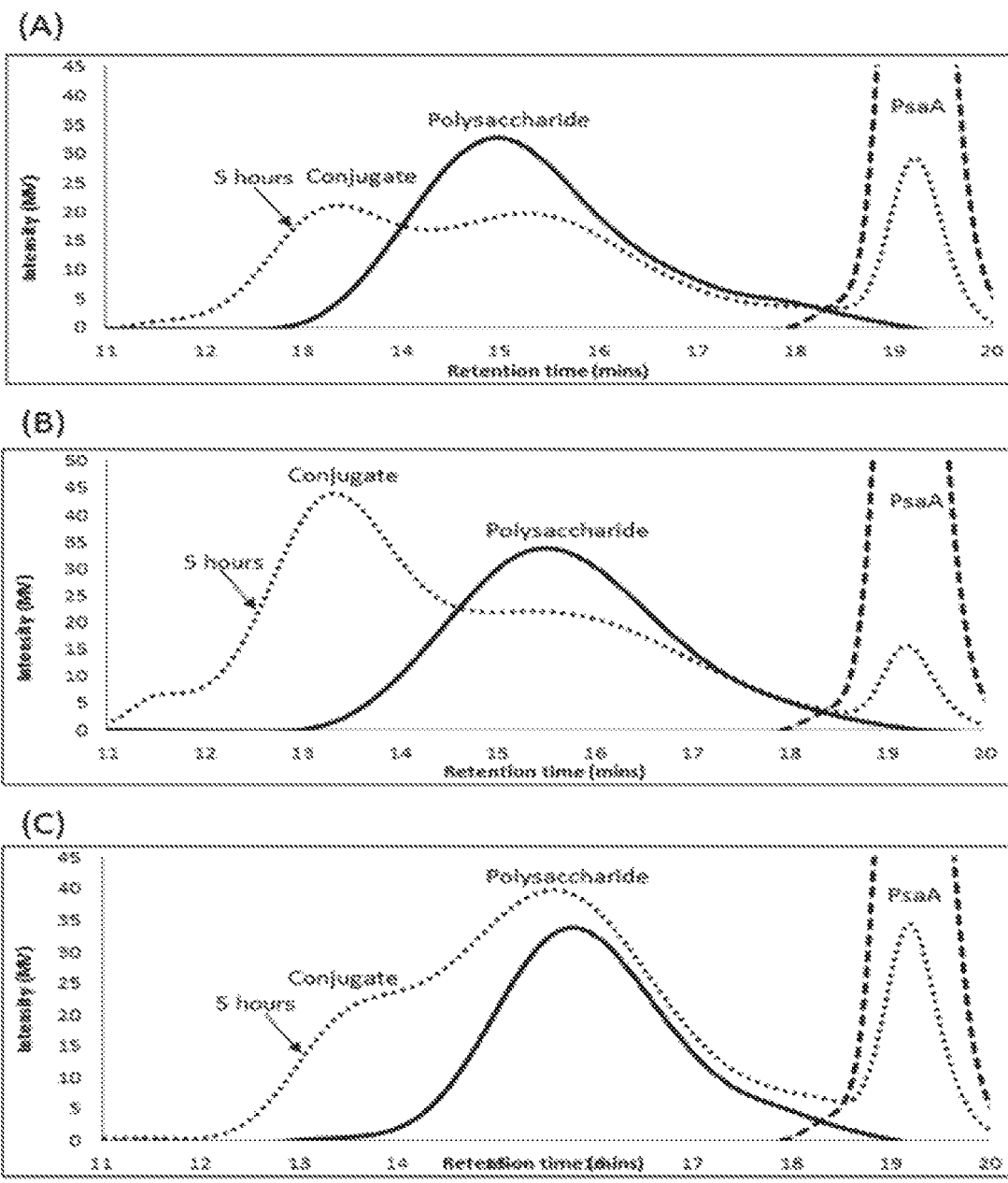
FIG. 2: An SEC-HPLC chromatogram illustrates conjugation reaction kinetics of serotype 5 (A), serotype 9V (B), serotype 18C (C), serotype 3 (D), serotype 6A (E), and serotype 6B (F).

SEC-HPLC chromatogram for conjugation reaction kinetics of Serotype 3 (D), 6A (E) and 6B (F) were performed. The following symbols were used for all three chromatograms; polysaccharide (solid line), PsaA (dashed line), 3 or 5 hour reaction (dotted line). As shown in FIG. 2 for all the chromatograms, the consumption of PsaA is indicated based on the reduction or disappearing the peak belongs PsaA at retention time of about 19 minutes. The conjugation is confirmed based on the formation of a new peak at about 13.5 minutes to about 14 minutes.

Conjugates of pneumococcal polysaccharides from serotype 5, 9V, 15B, 18C and 45 with PsaA were prepared using the procedure similar to the one described above. SEC-HPLC chromatogram for conjugation reaction kinetics of Serotype 5 (A), 9V (B) and 18C (C) was carried out. As shown in FIG. 2, all three chromatograms Polysaccharide (solid line), PsaA (dashed line), 3 or 5 hour reaction (dotted line). In all the chromatograms the consumption of PsaA is indicated based on the reduction or disappearing the peak belongs PsaA at retention time of about 19 mins. The conjugation is confirmed based on the formation of a new peak at about 13.5 minutes to about 14 minutes.

E) Activation and Conjugation of Pneumococcal Polysaccharide Serotype 8 to PsaA 1000 mg (200.0 mL of 5.0 mg/mL concentration) mechanically size reduced polysaccharide serotype 8 and 4.0 mL of CDAP (100 mg/mL in Acetonitrile (w/v)) was mixed in a glass bottle in the ratio of 1.0:0.4 (PS:CDAP) and stirred for 1 Min. The pH of the polysaccharide solution was adjusted to 9.0 with 8.0 mL of 0.2M triethylamine and stirred for 1 Min at room temperature (RT). 800 mg of PsaA (53.3 mL of 15.0 mg/mL concentration) was added slowly to the activated polysaccharide in a ratio of 1.0:0.8 (PnPs:PsaA).

Figure 6:
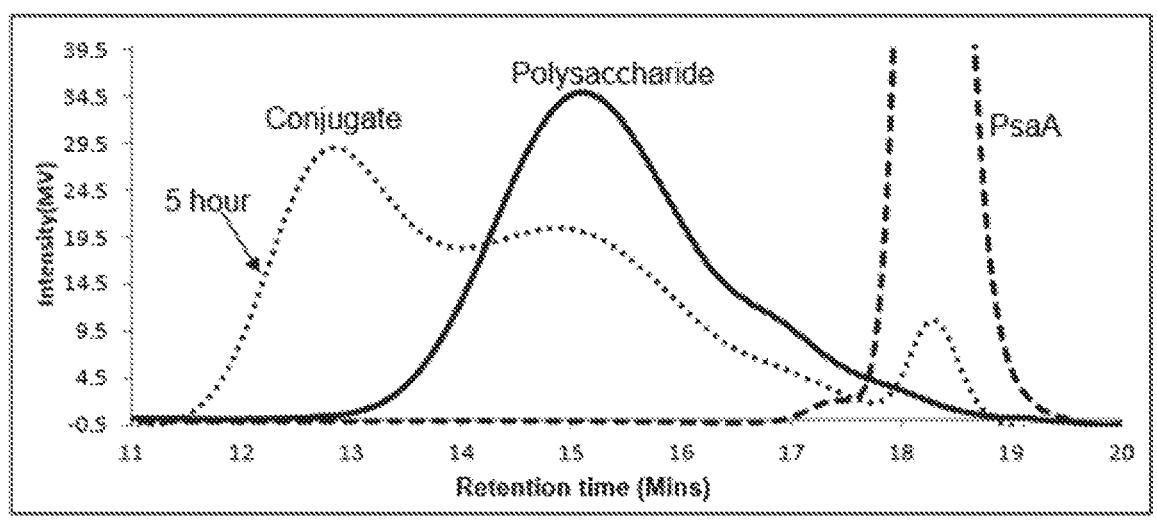
FIG. 6: An SEC-HPLC chromatogram illustrates conjugation reaction kinetics of serotype 8.

The pH of the reaction was adjusted to 9.0 with 2.0 mL of 0.2M triethylamine and the reaction was continued under stirring for 3-5 hours at room temperature followed by quenching of the reaction by adding excess concentration of glycine (100 mM). The conjugation kinetics of reactions were monitored using SEC-HPLC (FIG. 6) at each hour of the reaction.

F) Activation and Conjugation of Pneumococcal Polysaccharide Serotype 10 A to PsaA 1000 mg (142.8 mL of 7.0 mg/mL concentration) mechanically size reduced polysaccharide serotype 10A and 6.0 mL of CDAP (100 mg/mL in Acetonitrile (w/v)) was mixed in a glass bottle in the ratio of 1.0:0.6 (PS:CDAP) and stirred for 1 Min. The pH of the polysaccharide solution was adjusted to 9.0 with 7.5 mL of 0.2M triethylamine and stirred for 1 Min at room temperature (RT). 800 mg of PsaA (53.3 mL of 15.0 mg/mL concentration) was added slowly to the activated polysaccharide in a ratio of 1.0:0.8 (PnPs:PsaA).

Figure 7:
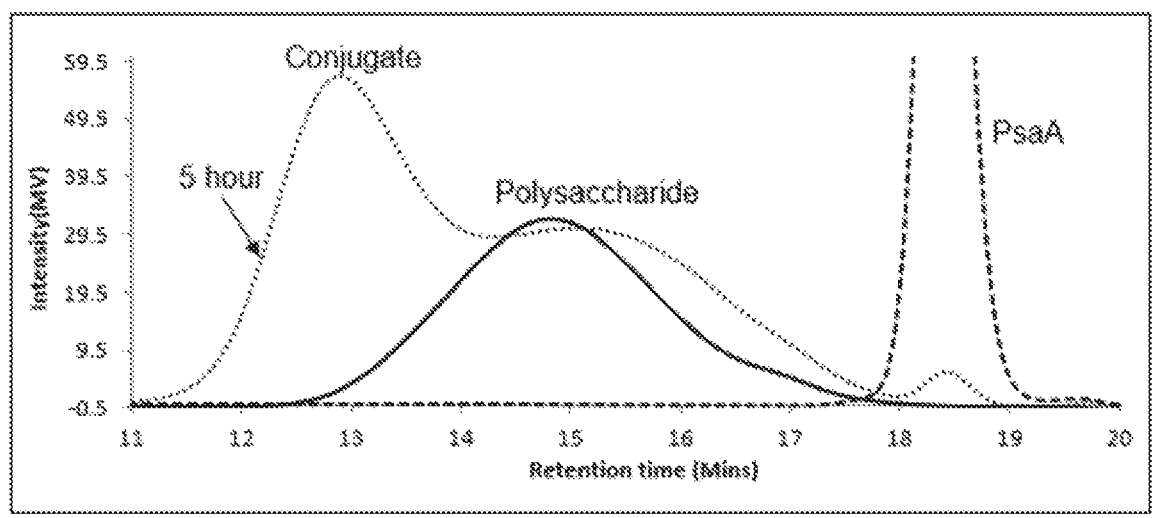
FIG. 7: An SEC-HPLC chromatogram illustrates conjugation reaction kinetics of serotype 10A.

The pH of the reaction was adjusted to 9.0 with 2.4 mL of 0.2M triethylamine and the reaction was continued under stirring for 3-5 hours at room temperature followed by quenching of the reaction by adding excess concentration of glycine (100 mM). The conjugation kinetics of reactions were monitored using SEC-HPLC (FIG. 7) at each hour of the reaction.

G) Activation and Conjugation of Pneumococcal Polysaccharide Serotype 11 A to PsaA 1000 mg (100.0 mL of 10.0 mg/mL concentration) mechanically size reduced polysaccharide serotype 11A and 8.0 mL of CDAP (100 mg/mL in Acetonitrile (w/v)) was mixed in a glass bottle in the ratio of 1.0:0.8 (PS:CDAP) and stirred for 1 Min. The pH of the polysaccharide solution was adjusted to 9.0 with 14.0 mL of 0.2M triethylamine and stirred for 1 Min at room temperature (RT). 800 mg of PsaA (53.3 mL of 15.0 mg/mL concentration) was added slowly to the activated polysaccharide in a ratio of 1.0:0.8 (PnPs:PsaA).

Figure 8:
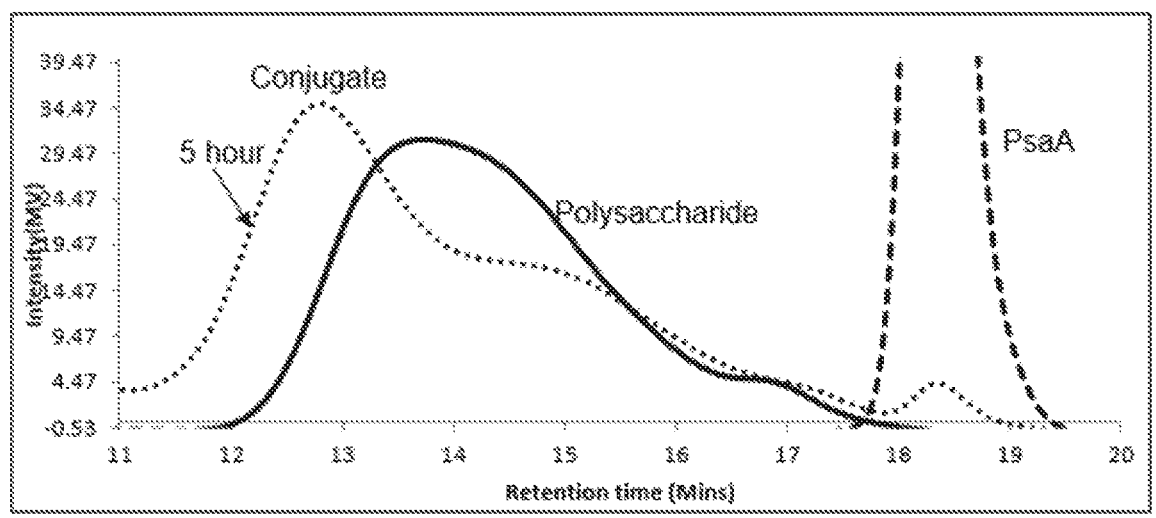
FIG. 8: An SEC-HPLC chromatogram illustrates conjugation reaction kinetics of serotype 11A.

The pH of the reaction was adjusted to 9.0 with 1.1 mL of 0.2M triethylamine and the reaction was continued under stirring for 3-5 hours at room temperature followed by quenching of the reaction by adding excess concentration of glycine (100 mM). The conjugation kinetics of reactions were monitored using SEC-HPLC (FIG. 8) at each hour of the reaction.H) Activation And Conjugation Of Pneumococcal Polysaccharide Serotype 12 F To PsaA 1000 mg (142.8 mL of 7.0 mg/mL concentration) mechanically size reduced polysaccharide serotype 12F and 4.0 mL of CDAP (100 mg/mL in Acetonitrile (w/v)) was mixed in a glass bottle in the ratio of 1.0:0.4 (PS:CDAP) and stirred for 1 Min. The pH of the polysaccharide solution was adjusted to 9.0 with 9.0 mL of 0.2M triethylamine and stirred for 1 Min at room temperature (RT). 700 mg of PsaA (46.6 mL of 15.0 mg/mL concentration) was added slowly to the activated polysaccharide in a ratio of 1.0:0.7 (PnPs:PsaA).

Figure 9:
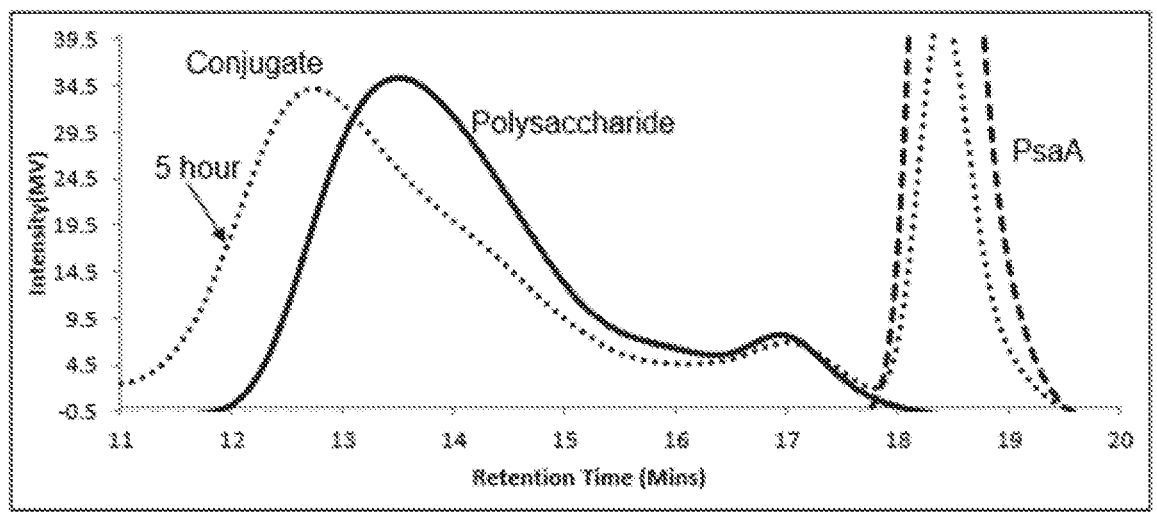
FIG. 9: An SEC-HPLC chromatogram illustrates conjugation reaction kinetics of serotype 12F.

The pH of the reaction was adjusted to 9.0 with 1.7 mL of 0.2M triethylamine and the reaction was continued under stirring for 3-5 hours at room temperature followed by quenching of the reaction by adding excess concentration of glycine (100 mM). The conjugation kinetics of reactions were monitored using SEC-HPLC (FIG. 9) at each hour of the reaction.

I) Activation and Conjugation of Pneumococcal Polysaccharide Serotype 15A to PsaA 1000 mg (71.4 mL of 14.0 mg/mL concentration) mechanically size reduced polysaccharide serotype 15A and 10.0 mL of CDAP (100 mg/mL in Acetonitrile (w/v)) was mixed in a glass bottle in the ratio of 1.0:1.0 (PS:CDAP) and stirred for 1 Min. The pH of the polysaccharide solution was adjusted to 9.0 with 20.5 mL of 0.2M triethylamine and stirred for 1 Min at room temperature (RT). 1000 mg of PsaA (66.6 mL of 15.0 mg/mL concentration) was added slowly to the activated polysaccharide in a ratio of 1.0:1.0 (PnPs:PsaA).

Figure 10:
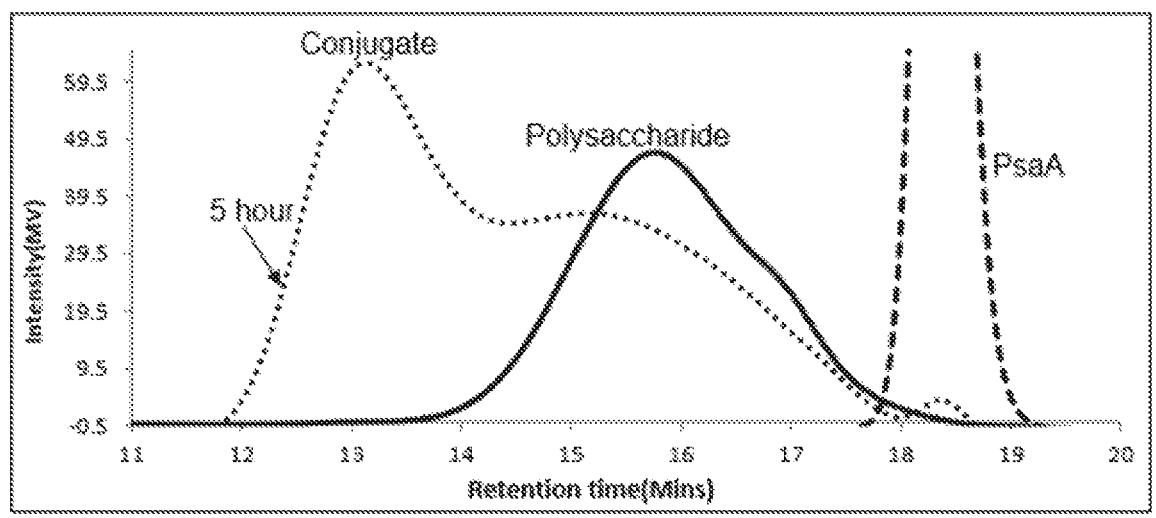
FIG. 10: An SEC-HPLC chromatogram illustrates conjugation reaction kinetics of serotype 15A.

The pH of the reaction was adjusted to 9.0 with 0.9 mL of 0.2M triethylamine and the reaction was continued under stirring for 3-5 hours at room temperature followed by quenching of the reaction by adding excess concentration of glycine (100 mM). The conjugation kinetics of reactions were monitored using SEC-HPLC (FIG. 10) at each hour of the reaction.

J) Activation and Conjugation of Pneumococcal Polysaccharide Serotype 23 A to PsaA 1000 mg (83.3 mL of 12.0 mg/mL concentration) mechanically size reduced polysaccharide serotype 23A and 10.0 mL of CDAP (100 mg/mL in Acetonitrile (w/v)) was mixed in a glass bottle in the ratio of 1.0:1.0 (PS:CDAP) and stirred for 1 Min. The pH of the polysaccharide solution was adjusted to 9.0 with 20.3 mL of 0.2M triethylamine and stirred for 1 Min at room temperature (RT). 600 mg of PsaA (40.0 mL of 15.0 mg/mL concentration) was added slowly to the activated polysaccharide in a ratio of 1.0:0.6 (PnPs:PsaA).

Figure 11:
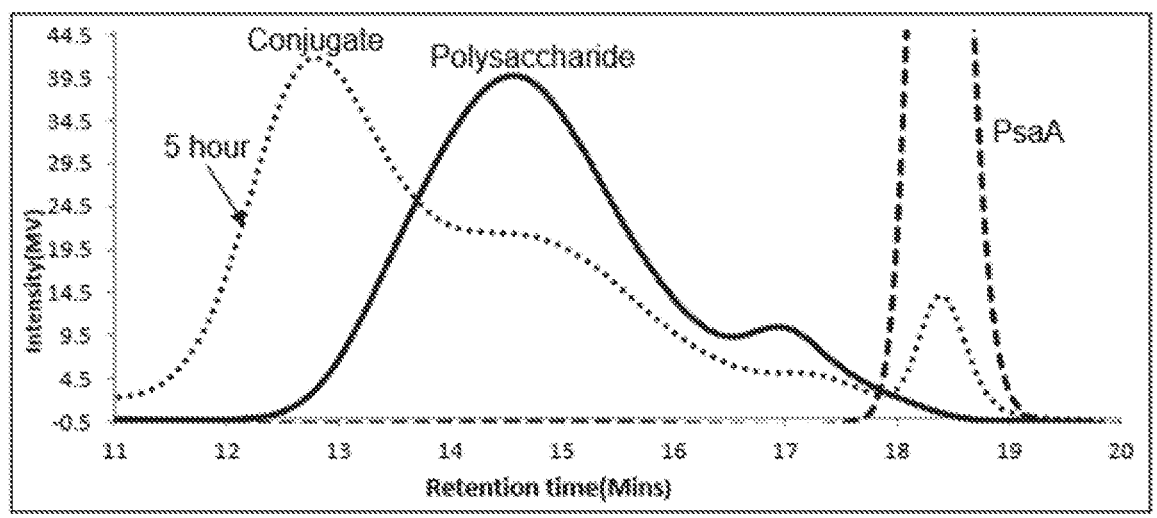
FIG. 11: An SEC-HPLC chromatogram illustrates conjugation reaction kinetics of serotype 23A.

The pH of the reaction was adjusted to 9.0 with 1.1 mL of 0.2M triethylamine and the reaction was continued under stirring for 3-5 hours at room temperature followed by quenching of the reaction by adding excess concentration of glycine (100 mM). The conjugation kinetics of reactions were monitored using SEC-HPLC (FIG. 11) at each hour of the reaction.

K) Activation and Conjugation of Pneumococcal Polysaccharide Serotype 23 B to PsaA 1000 mg (100.0 mL of 10.0 mg/mL concentration) mechanically size reduced polysaccharide serotype 23B and 2.0 mL of CDAP (100 mg/mL in Acetonitrile (w/v)) was mixed in a glass bottle in the ratio of 1.0:0.2 (PS:CDAP) and stirred for 1 Min. The pH of the polysaccharide solution was adjusted to 9.0 with 3.0 mL of 0.2M triethylamine and stirred for 1 Min at room temperature (RT). 1000 mg of PsaA (66.6 mL of 15.0 mg/mL concentration) was added slowly to the activated polysaccharide in a ratio of 1.0:1.0 (PnPs:PsaA).

Figure 12:
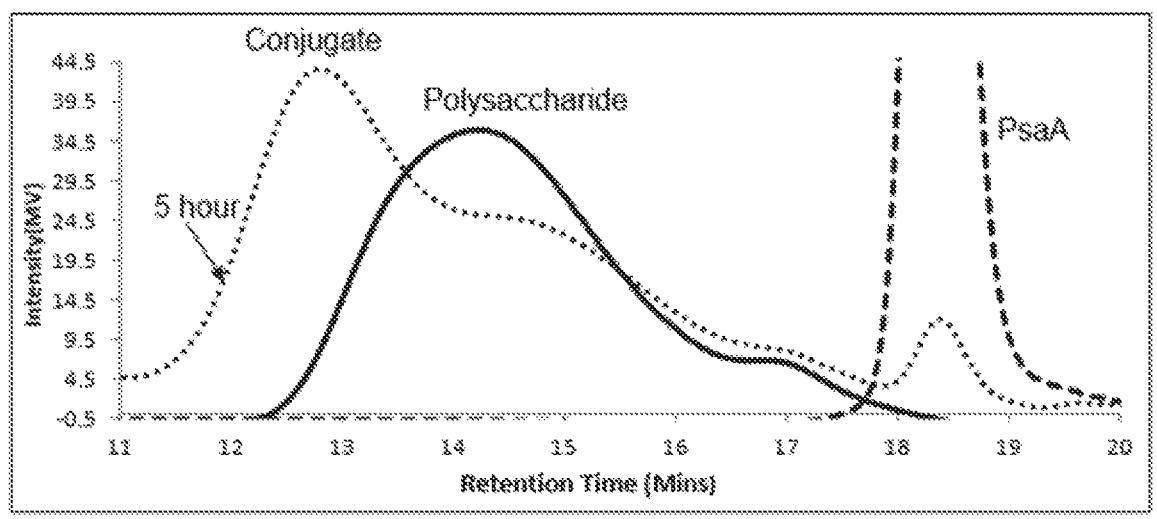
FIG. 12: An SEC-HPLC chromatogram illustrates conjugation reaction kinetics of serotype 23B.

The pH of the reaction was adjusted to 9.0 with 2.4 mL of 0.2M triethylamine and the reaction was continued under stirring for 3-5 hours at room temperature followed by quenching of the reaction by adding excess concentration of glycine (100 mM). The conjugation kinetics of reactions were monitored using SEC-HPLC (FIG. 12) at each hour of the reaction.

L) Activation and Conjugation of Pneumococcal Polysaccharide Serotype 24 F to PsaA 1000 mg (125.0 mL of 8.0 mg/mL concentration) mechanically size reduced polysaccharide serotype 24F, and 3.0 mL of CDAP (100 mg/mL in Acetonitrile (w/v)) was mixed in a glass bottle in the ratio of 1.0:0.3 (PS:CDAP) and stirred for 1 Min. The pH of the polysaccharide solution was adjusted to 9.0 with 10.0 mL of 0.2M triethylamine and stirred for 1 Min at room temperature (RT). 600 mg of PsaA (40.0 mL of 15.0 mg/mL concentration) was added slowly to the activated polysaccharide in a ratio of 1.0:0.6 (PnPs:PsaA).

Figure 13:
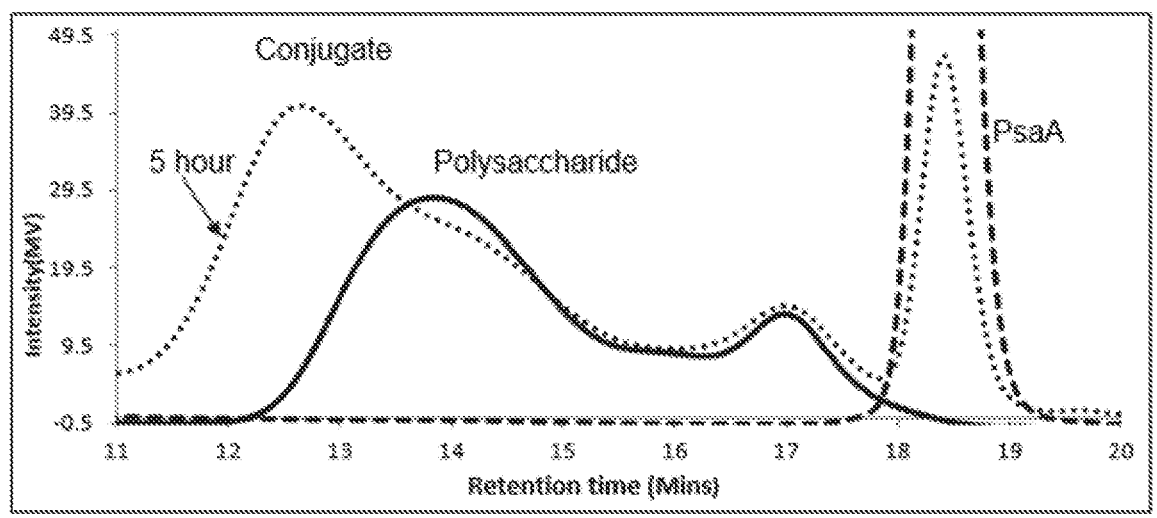
FIG. 13: An SEC-HPLC chromatogram illustrates conjugation reaction kinetics of serotype 24F.

The pH of the reaction was adjusted to 9.0 with 3.5 mL of 0.2M triethylamine and the reaction was continued under stirring for 3-5 hours at room temperature followed by quenching of the reaction by adding excess concentration of glycine (100 mM). The conjugation kinetics of reactions were monitored using SEC-HPLC (FIG. 13) at each hour of the reaction.

M) Activation and Conjugation of Pneumococcal Polysaccharide Serotype 35 B to PsaA 1000 mg (142.8 mL of 7.0 mg/mL concentration) mechanically size reduced polysaccharide serotype 35B and 6.0 mL of CDAP (100 mg/mL in Acetonitrile (w/v)) was mixed in a glass bottle in the ratio of 1.0:0.6 (PS:CDAP) and stirred for 1 Min. The pH of the polysaccharide solution was adjusted to 9.0 with 7.0 mL of 0.2M triethylamine and stirred for 1 Min at room temperature (RT). 1000 mg of PsaA (66.6 mL of 15.0 mg/mL concentration) was added slowly to the activated polysaccharide in a ratio of 1.0:1.0 (PnPs:PsaA).

Figure 14:
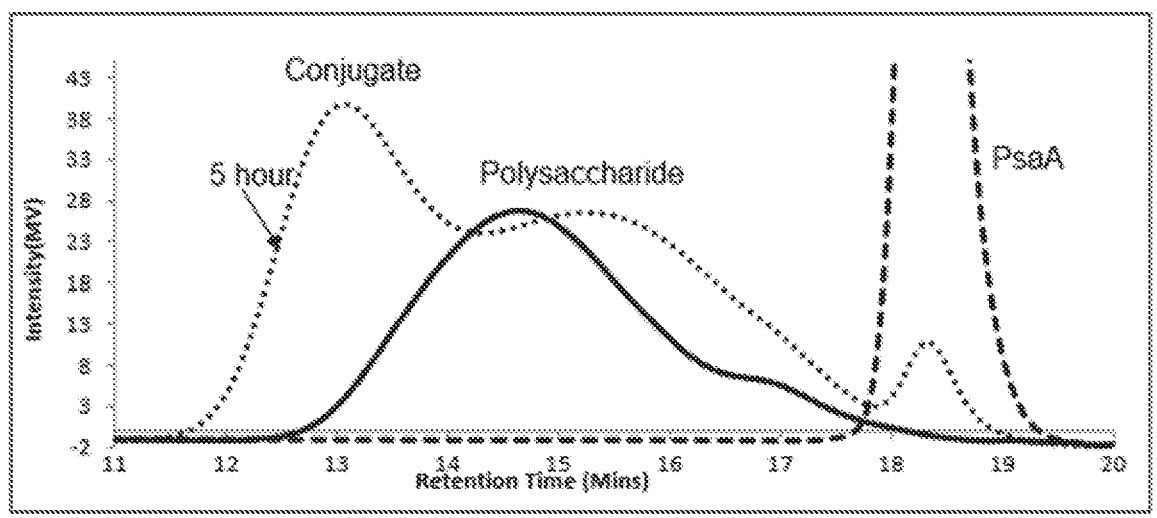
FIG. 14: An SEC-HPLC chromatogram illustrates conjugation reaction kinetics of serotype 35B.

The pH of the reaction was adjusted to 9.0 with 2.2 mL of 0.2M triethylamine and the reaction was continued under stirring for 3-5 hours at room temperature followed by quenching of the reaction by adding excess concentration of glycine (100 mM). The conjugation kinetics of reactions were monitored using SEC-HPLC (FIG. 14) at each hour of the reaction.

Example 2: Preparation of Pneumococcal Capsular Polysaccharide-$CRM_{197}$ Conjugates A) Activation of Polysaccharide and Conjugation with Carrier Protein:

Sized polysaccharide (6.0 mL of Ps, concentration of 10 mg/mL) and CDAP (100 mg/mL in Acetonitrile (w/v)) was mixed in a glass vial in the ratio of 1:1 and stirred for 1 min. The pH of the polysaccharide solution was adjusted to 9.25 with 0.2M triethylamine and stirred for 3 min at room temperature (RT). $CRM_{197}$ (4.0 mL of conc. 15.0 mg/mL) was added slowly to the activated polysaccharide in a ratio of 1:1 (Ps:Carrier protein).

The pH of the reaction were adjusted to about 9.05 with 0.2M triethylamine and the reaction was continued under stirring for 5 hours at room temperature and finally the reaction was quenched by adding excess concentration of glycine.

The reaction mixture was diafiltered using 100 K MWCO membrane and purified by size-exclusion chromatography. The fractions were analyzed by SEC-MALLS, anthrone method and fractions containing conjugates were pooled and sterile filtered with 0.2μ filters. This material is called monovalent conjugate bulk.

The reaction kinetics of the conjugates prepared from serotypes 7F (A), 14 (B) and 19F (C) with $CRM_{197}$ were prepared and the reaction kinetics are shown in FIG. 1. In all three chromatograms polysaccharide (solid line), $CRM_{197}$ (dashed line), 5 hour reaction (dotted line). In all the chromatograms the consumption of $CRM_{197}$ is indicated based on the reduction or disappearing the peak belongs $CRM_{197}$ at retention time of about 19 minutes. The conjugation is confirmed based on the formation of a new peak at about 13.5 minutes to about 14 minutes.

The reaction kinetics of the conjugates prepared from serotypes 3 (D), 6A (E) and 6B (F) with $CRM_{197}$ were prepared and the reaction kinetics are shown in FIG. 1. In all three chromatograms polysaccharide (solid line), $CRM_{197}$ (dashed line), 5 hour reaction (dotted line). In all the chromatograms the consumption of $CRM_{197}$ is indicated based on the reduction or disappearing the peak belongs $CRM_{197}$ at retention time of about 19 minutes. The conjugation is confirmed based on the formation of a new peak at about 13.5 minutes to about 14 minutes.

Example 3: Formulation of Pneumococcal Capsular Polysaccharide-Protein Conjugate Vaccine A 15 valent conjugated vaccine was formulated as 0.5 mL dose containing 2.2 μg of each pneumococcal polysaccharide from serotypes 1, 4, 5, 7F, 9V, 14, 18C, 19A, 19F, 22F, 23F & 33F conjugated to ~28 μg $CRM_{197}$ Protein and 2.2 μg of each polysaccharide from serotypes 3, 6A and 6B conjugated to about 7 μg PsaA Protein. All the conjugates were adsorbed on to aluminum phosphate gel equivalent to 0.5 mg $Al^{3+}$ per dose of 0.5 mL. The 0.9% W/V saline was used as diluent and vehicle for the formulation and the final formulation pH was adjusted to pH 6 using 1N hydrochloric acid. For effective adsorption post adjusting the pH, the formulation was mixed for 2 hours under constant stirring. After 2 hours of blending, the formulated blend was aseptically filled at 0.58 mL fill volume per vial into the 3 mL sterile nonsiliconized vials, closed with sterile 13 mm rubber stoppers and sealed with 13 mm sterile pink colored flip off aluminum seals, followed by optical inspection and labelling of filled vials. From the lot, some vials randomly picked were sent for analyzing the appearance, pH, Osmolality, total poly and protein content (μg/SHD), % Adsorption, aluminum content (mg/SHD).

Example 4: Formulation of Pneumococcal Capsular Polysaccharide-Protein Conjugate Vaccine A 15 valent conjugated vaccine was formulated as 0.5 mL dose containing 2.2 μg of each polysaccharide from serotypes 1, 4, 5, 7F, 9V, 14, 18C, 19A, 19F, 22F, 23F & 33F conjugated to ~28 μg $CRM_{197}$ protein and 4.4 μg of each polysaccharide from serotypes 3, 6A and 6B conjugated to ~14 μg PsaA Protein. All the conjugates were adsorbed on to aluminum phosphate gel equivalent to 0.5 mg $Al^{3+}$ per dose of 0.5 mL. The 0.9% w/v saline was used as diluent and vehicle for the formulation and the final formulation pH was adjusted to pH 6 using 1N hydrochloric acid. For effective adsorption post adjusting the pH, the formulation was mixed for 2 hours under constant stirring. After 2 hours of blending, the formulated blend was aseptically filled at 0.58 mL fill volume per vial into the 3 mL sterile nonsiliconized vials, closed with sterile 13 mm rubber stoppers and sealed with 13 mm sterile pink colored flip off aluminum seals, followed by optical inspection and labelling of filled vials. From the lot, some vials randomly picked were sent for analyzing the appearance, pH, Osmolality, Total poly and protein content (μg/SHD), % Adsorption, aluminum content (mg/SHD).

A) Immunization of Rabbits with the Formulated Vaccine

Healthy rabbits 1.5 to 2 kg each were bred and reared in a specific pathogen free contained facility. Rabbits were immunized with the aforementioned formulation with the following schedule.

Group 1 consisted of 7 rabbits that were immunized with the 15 valent conjugate vaccine (Example 3). The 15 valent vaccine comprised of 2.2 μg each of the S. pneumoniae polysaccharides of serotypes 1, 4, 5, 7F, 9V, 14, 18C, 19A, 19F, 22F, 23F, 33F conjugated to $CRM_{197}$ and 2.2 μg each S. pneumoniae polysaccharides of serotypes 3, 6A and 6B conjugated to PsaA. Rabbits were immunized on days 1, 15 and 29; blood samples were collected on days 0, 15 and 36. Serum was separated from the blood sample and stored at −80° C.

Figure 4:
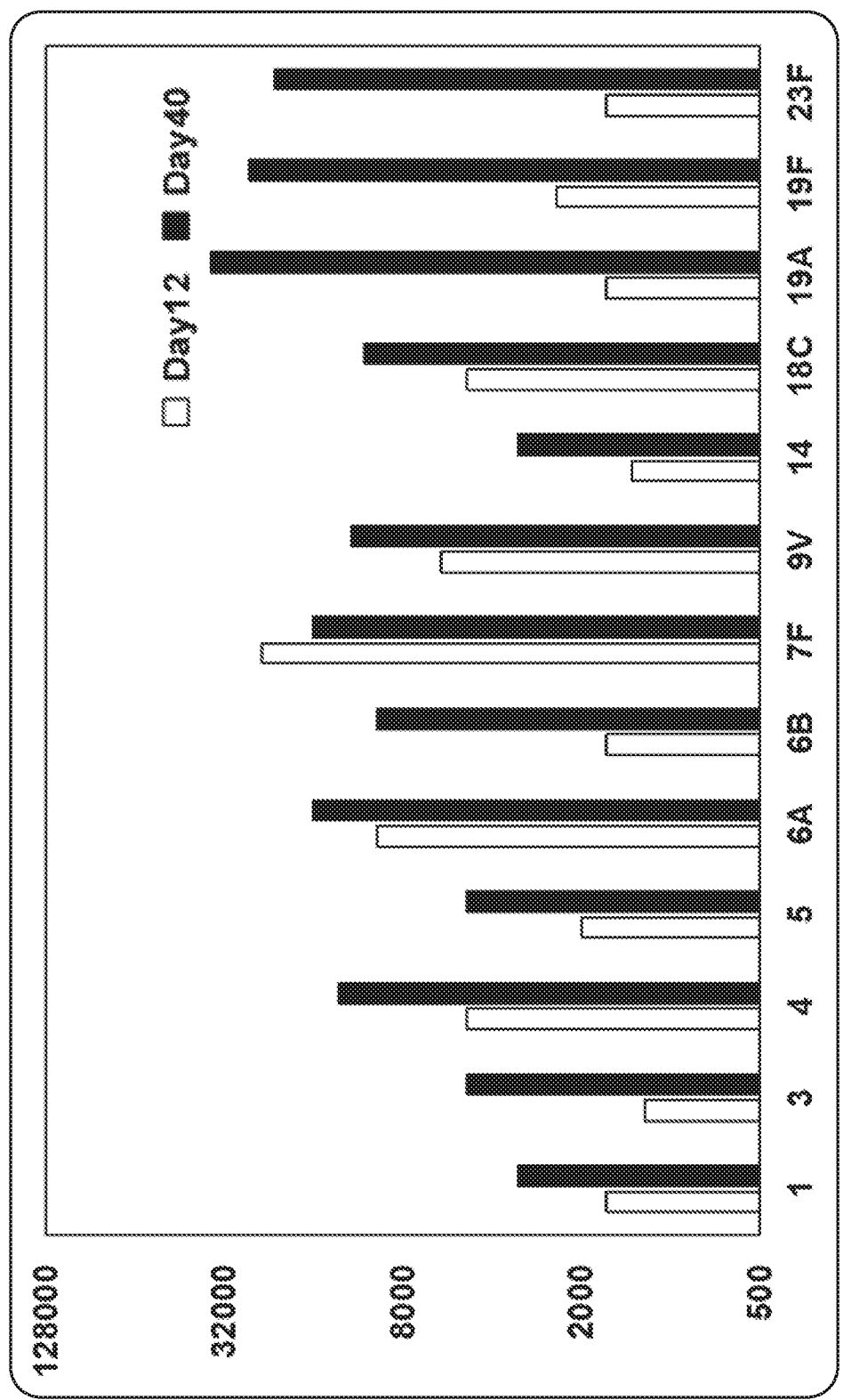
FIG. 4: Immune response to different serotypes in rabbits immunized with Prevnar 13®.

Group 2 consists of 7 rabbits that were immunized with the 13 valent conjugate vaccine—Prevnar13®. Rabbits were immunized on days 1, 15 and 29; blood samples were collected on days 0, 12, 26 and 40. Data from day 12 and day 40 was used to plot for comparison with the PsaA study (FIG. 4). Serum was separated from the blood sample and stored at −80° C.

Group 3 consists of 7 rabbits that were immunized with the 15 valent conjugate vaccine (Example 4). The 15 valent vaccine comprised of 2.2 μg of polysaccharide for each serotypes 1, 4, 5, 7F, 9V, 14, 18C, 19A, 19F, 22F, 23F & 33F conjugated to ~28 μg $CRM_{197}$ protein and 4.4 μg of each polysaccharide for Serotypes 3, 6A and 6B conjugated to ~14 μg PsaA protein. Rabbits were immunized on days 1, 15 and 29; blood samples were collected on days 0, 15 and 36. Serum was separated from the blood sample and stored at −80° C. Serum obtained from the immunized rabbits were analyzed for serotype specific immune response using ELISA.

The ELISA was performed as per the WHO suggested protocol. Briefly, Maxisorp™ ELISA plates were coated with PnCPS of given serotype (1 μg/50 μL/well using PBS;

sterile endotoxin free, with 0.02% sodium azide). Plates were placed in a box with moistened paper towels for humidification and incubated at 37° C.±2° C. for 5 hrs, the plates were then stored at 5° C.±3° C. until use.

The test sera were pre-adsorbed to CWPS Mlti™ to eliminate background reactivity originating from cell-wall polysaccharide. To achieve this 2 μL of test and positive control serum were diluted using 998 μL preadsorption solution (1 mL-1 μL CWPS Multi™ in 999 μL of 10% SuperBlock™ in PBST) to get final dilution of 1:500. The diluted samples were incubated at room temperature (25° C.±5° C.) for 1 hr with continuous shaking. The unbound PnCPS were removed by flicking the plate and the free sites in the wells were blocked by adding 200 μL of blocker (20% SuperBlock™ in PBS). The plate were incubated at room temperature (25° C.±5° C.) for 1 hr without shaking.

B) Test Samples and Controls Addition

50 μL diluent (10% SuperBlock™ in PBST) were added to all wells except A1 to A12. Following this 100 μL/well preabsorbed test sera samples were added to A1 to A10, control sera samples were added to A11 and A12. Two fold serial dilution of test samples was performed by transferring 50 μL from $1^{st}$ to $2^{nd}$ and so on i.e. from A1-A10 to H1-H10. Similarly, serial dilution of control samples (007SP) from A11 and 12 to E11 and E12 were performed. F11 and F12 to H11 and H12 without dilution were set up as blank.

The plates were incubated at room temperature (25° C.±5° C.) for 2 hrs without shaking. Following the incubation step the contents were discarded and the plates were washed thrice with PBST (0.250 μL/well) manually or with plate washer.

C) Primary Antibody Addition

50 μL/well recombinant protein A/G peroxidase (diluted 1:20000 using 10% SuperBlock™ in PBST) was added to all wells and the plates were incubated for 1 hr at room temperature (25° C.±5° C.) without shaking. Following this, the plates were washed thrice with PBST (250 μL/well) manually or with plate washer.

D) Development and Reading

Chromogenic reaction was developed by adding 50 μL/well TMB substrate and incubated for 15 mins at room temperature (25° C.±5C) without shaking. The reaction was stopped by adding 50 μl/well 1.25M Sulphuric acid. The OD at 450 nm was measured.

E) Titer Estimation

Antibody titer in the immunized animals were assigned as inverse of dilution factor. The highest dilution showing $OD_{450}$ nm as twice the pre-immune titer (approximately 0.2) was reported as titer. The titer of serum antibody to each serotype was plotted and compared with different treatment groups.

Figure 3:
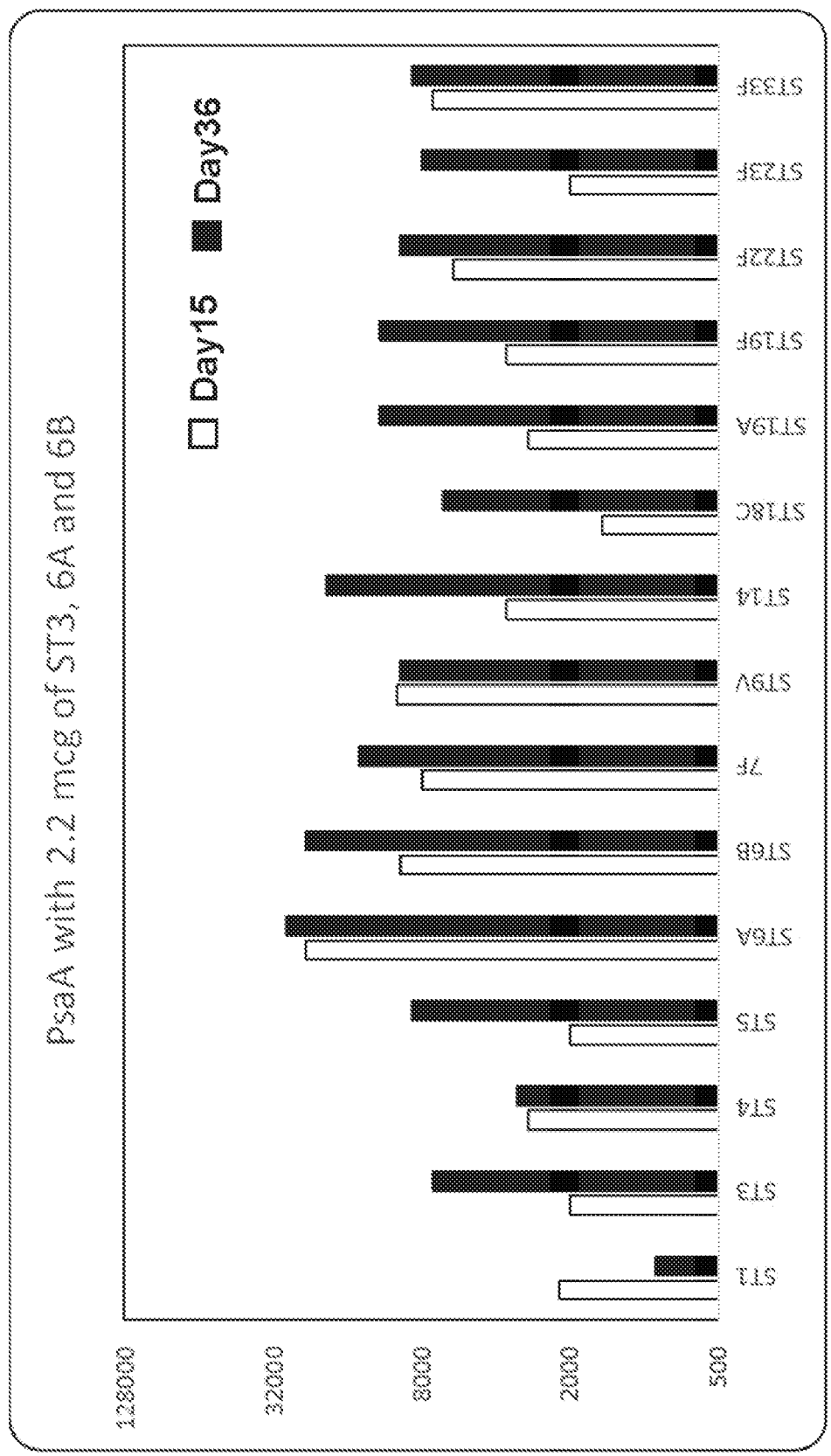
FIG. 3: Immune response to different serotypes in rabbits immunized with a composition of the present disclosure as described in Example 3.
Figure 5:
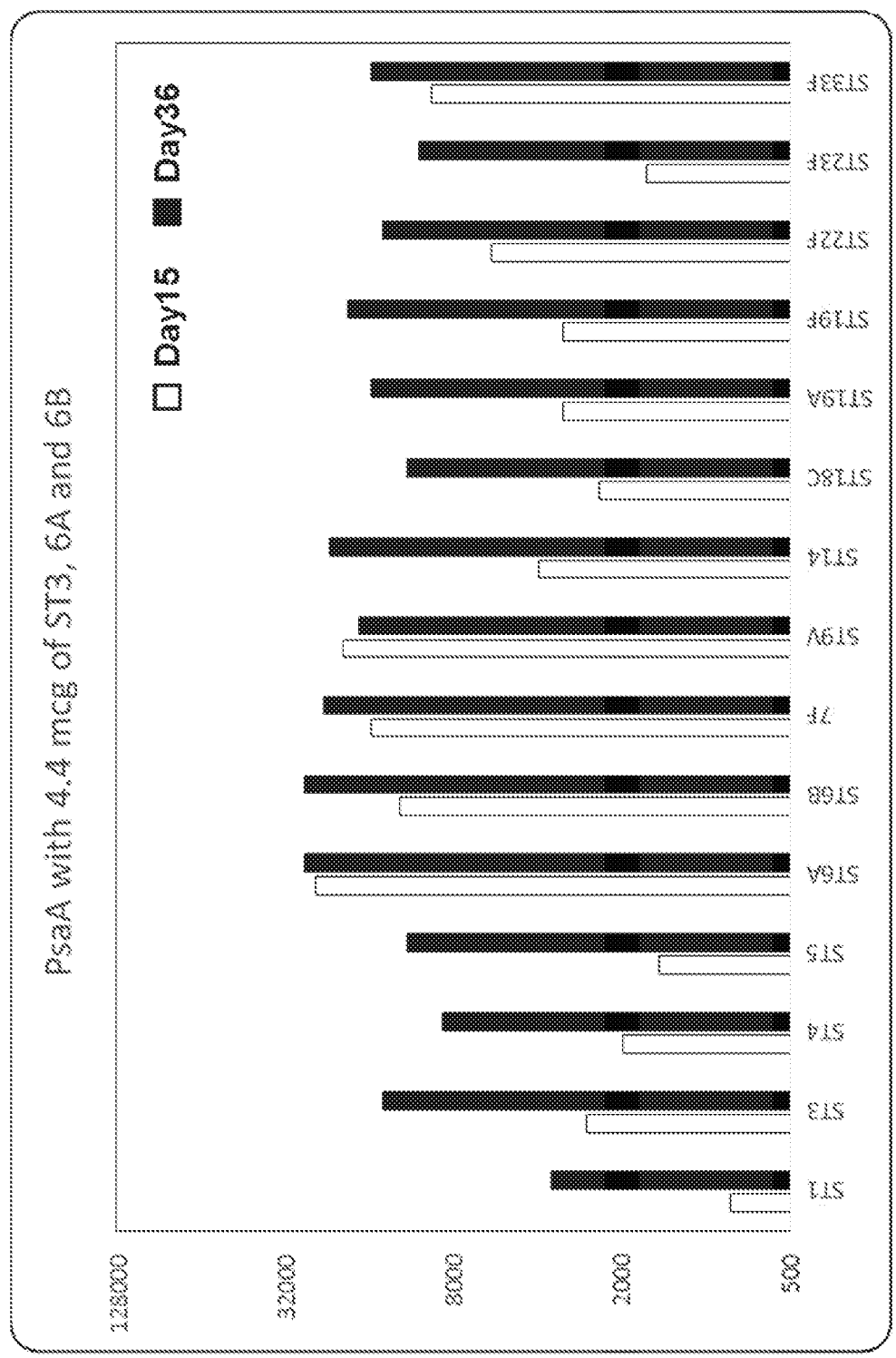
FIG. 5: Immune response to different serotypes in rabbits immunized with another composition of the present disclosure as described in Example 4.

The immune response data of animals from Group 1 shows dose dependent rise in serotype specific rise in serum antibody titer i.e. the level of antibody titer increased with each subsequent dose in the vaccinated animals. The immune response to Serotype 3 (FIG. 5) was about 1:10000 when the animals were immunized with conjugates of PsaA containing 4.4 μg of polysaccharide (group 3). Further, the serum antibody titer to serotypes 3, 6A and 6B were at least twice as much when compared to the immune response obtained from Prevnar®13 immunized rabbits. The serum IgG titer after first immunization in rabbits with Prevnar®13 does not show rise to the same extent as observed with the 15 valent formulation of the present disclosure (FIGS. 3 & 4). Even though the concentration of polysaccharide for serotype 6B in Prevnar®13 is twice as much (4.4 μg), when compared to the concentration of serotype 3 polysaccharide conjugated to PsaA (FIG. 3), is twice the level of IgG response. The titer of Serotype 3 antibody barely reaches 8000 in formulations containing 2.2 μg of Serotype 3 conjugated to $CRM_{197}$. This titer shows a notable improvement (16000) when conjugated to 4.4 μg of PsaA. This is an improvement in the immune response due to conjugation of serotype 3, 6A and 6B polysaccharides to PsaA. Serum antibody titer to serotype 14 in Prevnar®13 vaccinated animals were lower when compared to the formulations of the present disclosure. IgG response to other serotypes in animal vaccinated either with the vaccine formulations of the present disclosure or with Prevnar®13 were similar. Serotypes 3, 6A and 6B titers were improved upon conjugation to PsaA even at 2.2 μg concentration.

The use of numerical values specified in this application, unless expressly indicated otherwise, are stated as approximations through the minimum and maximum values specified within the stated ranges, and preceded by the word "about." The disclosure of ranges is intended as a continuous range including every value between the minimum and maximum values recited as well as any ranges that may be formed through such values. The numerical values presented in this application represent various embodiments of the present disclosure.

Throughout this disclosure, the singular terms "a," "an," and "the" include plural referents unless the context clearly indicates otherwise. Similarly, unless the word "or" is expressly limited to mean only a single item exclusive from the other items in reference to a list of two or more items, then the use of "or" in such a list is to be interpreted as including (a) any single-item in the list, (b) all of the items in the list, or (c) any combination of the items in the list. Additionally, the terms "comprising" and the like are used throughout this disclosure to mean including at least the recited feature(s) such that any greater number of the same feature(s) and/or one or more additional types of features are not precluded. Reference herein to "one embodiment," "an embodiment," or similar formulations means that a particular feature of a composition, a composition, a method, or a characteristic described in connection with the embodiment may be included in at least one embodiment of the present technology. Thus, the appearances of such phrases or formulations herein are not necessarily all referring to the same embodiment. Furthermore, various particular features, compositions, methods, or characteristics may be combined in any suitable manner in one or more embodiments.

This disclosure is not intended to be exhaustive or to limit the present technology to the precise forms disclosed herein. Although specific embodiments are disclosed herein for illustrative purposes, various equivalent modifications are possible without deviating from the present technology, as those of ordinary skill in the relevant art will recognize. In some cases, well-known structures and functions have not been shown and/or described in detail to avoid unnecessarily obscuring the description of the embodiments of the present technology. Although steps of methods may be presented herein in a particular order, in alternative embodiments the steps may have another suitable order. Similarly, certain embodiments of the present technology disclosed in the context of particular embodiments may be combined or eliminated in other embodiments. Furthermore, while advantages associated with certain embodiments may have been disclosed in the context of those embodiments, other embodiments may also exhibit such advantages, and not all embodiments need necessarily exhibit such advantages or other advantages disclosed herein to fall within the scope of the present technology. Accordingly, this disclosure and associated technology may encompass other embodiments not expressly shown and/or described herein.

From the foregoing, it will be appreciated that specific embodiments of the disclosure have been described herein for purposes of illustration, but that various modifications may be made without deviating from the scope of the disclosure. Accordingly, the disclosure is not limited except as by the appended claims.

What is claimed is:

1. A multivalent pneumococcal vaccine composition comprising:
   (a) carrier proteins consisting of pneumococcal surface adhesion protein A (PsaA) and $CRM_{197}$; and
   (b) capsular pneumococcal polysaccharides of two or more serotypes,
   wherein each of the capsular pneumococcal polysaccharides are individually conjugated to a carrier protein selected from PsaA and $CRM_{197}$,
   wherein at least one capsular pneumococcal polysaccharide is conjugated to PsaA,
   wherein at least one capsular pneumococcal polysaccharide is conjugated to $CRM_{197}$,
   wherein the at least one capsular pneumococcal polysaccharide conjugated to PsaA has a serotype different from a serotype of the at least one capsular pneumococcal polysaccharide conjugated to $CRM_{197}$ and
   wherein the PsaA lacks the wild-type hydrophobic N-terminal leader peptide.

2. The multivalent pneumococcal vaccine composition of claim 1, wherein the pneumococcal vaccine composition is a 10 valent, 13 valent, 14 valent, 15 valent, 17 valent, 18 valent, 19 valent, 20 valent, 22 valent, 23 valent, 24 valent or 25 valent pneumococcal vaccine composition.

3. The multivalent pneumococcal vaccine composition of claim 1, the two or more serotypes are selected from the group consisting of 1, 2, 3, 4, 5, 6A, 6B, 6C, 7F, 8, 9N, 9V, 10A, 11A, 12F, 14, 15A, 15B, 15C, 16F, 17F, 18C, 19F, 19A, 20A, 20B, 22F, 23A, 23B, 23F, 24B, 24F, 31, 33F, 34, 35B, 35F, 38, 39 and 45.

4. The multivalent pneumococcal vaccine composition of claim 1 having a percent ratio of carrier proteins to capsular pneumococcal polysaccharides (protein/PS) of about 0.5 to about 2.0 protein/PS.

5. The multivalent pneumococcal vaccine composition of claim 1 further comprising a pharmaceutically acceptable carrier.

6. The multivalent pneumococcal composition of claim 1, further comprising capsular pneumococcal polysaccharides of 10 or more serotypes selected from the group consisting of 1, 2, 3, 4, 5, 6A, 6B, 6C, 7F, 8, 9N, 9V, 10A, 11A, 12F, 14, 15A, 15B, 15C, 16F, 17F, 18C, 19F, 19A, 20A, 20B, 22F, 23A, 23B, 23F, 24B, 24F, 31, 33F, 34, 35B, 35F, 38, 39 and 45.

7. The pneumococcal vaccine composition of claim 1 wherein the pneumococcal vaccine composition comprises at least 14 pneumococcal polysaccharides, at least 17 pneumococcal polysaccharides, at least 19 pneumococcal polysaccharides, at least 20 pneumococcal polysaccharides, at least 22 pneumococcal polysaccharides, or at least 24 pneumococcal polysaccharides.

8. The pneumococcal vaccine composition of claim 1 comprising (1) pneumococcal polysaccharides of two or more serotypes and a carrier protein, wherein the serotypes are selected from 1, 3, 4, 5, 6A, 6B, 7F, 9V, 14, 18C, 19F, 19A and 22F and the carrier protein is PsaA or (2) pneumococcal polysaccharides of two or more serotypes and a carrier protein, wherein the serotypes are selected from 1, 3, 4, 5, 6A, 6B, 7F, 9V, 10A, 12F, 14, 15A, 15B, 18C, 19F, 19A, 22F, 23F, 33F, 34, 35, 38 and 45, and the carrier protein is PsaA.

9. The multivalent pneumococcal vaccine composition of claim 1, wherein the multivalent pneumococcal vaccine composition is formulated into a dosage unit.

10. The multivalent pneumococcal vaccine composition of claim 9, wherein the dosage unit comprises about 0.1 µg to about 50 µg, about 0.1 µg to about 10 µg, or about 1 µg to about 5 µg of each capsular pneumococcal polysaccharide, and wherein each of the capsular pneumococcal polysaccharides is individually conjugated to about 1.5 µg to about 5 µg of carrier protein.

11. The multivalent pneumococcal vaccine composition of claim 1 further comprising a pharmaceutically acceptable diluent, buffer, preservative, stabilizer, adjuvant, and/or a lyophilization excipient.

12. The multivalent pneumococcal vaccine composition of claim 9, wherein the dosage unit is supplied as a unit dose vial, a multiple dose vial, or a pre-filled syringe.

13. The pneumococcal vaccine composition of claim 1 wherein the pneumococcal vaccine composition is a single 0.5 mL dose comprising:
   about 2.2 to 4.4 µg of one or more pneumococcal polysaccharides;
   about 1 µg to about 10 µg of PsaA conjugated to each of the one or more pneumococcal polysaccharides;
   about 1 µg to about 10 µg of $CRM_{197}$ conjugated to each of the one or more pneumococcal polysaccharides;
   about 0.2 mg to about 1 mg of aluminum phosphate adjuvant; and
   an excipient.

14. A method of inducing an immune response in a subject comprising, administering an effective amount of the multivalent pneumococcal vaccine composition of claim 1 to the subject.

15. The method of claim 14, wherein the subject has a disease mediated by *Streptococcus pneumoniae*.

16. The method of claim 15, wherein the disease mediated by *Streptococcus pneumoniae* is invasive pneumococcal disease (IPD).

* * * * *